(12) United States Patent
Machida

(10) Patent No.: US 7,006,591 B2
(45) Date of Patent: Feb. 28, 2006

(54) COMPUTED TOMOGRAPHY APPARATUS AND PROGRAM

(75) Inventor: Yoshio Machida, Nasu-Gun (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 76 days.

(21) Appl. No.: 10/656,277

(22) Filed: Sep. 8, 2003

(65) Prior Publication Data
US 2004/0066879 A1   Apr. 8, 2004

(30) Foreign Application Priority Data
Sep. 9, 2002  (JP) ............................. 2002-262926

(51) Int. Cl.
    A61B 6/03    (2006.01)
(52) U.S. Cl. ............................. 378/4; 378/19; 378/17; 378/901
(58) Field of Classification Search ............... 378/4, 378/8, 15, 17, 19, 901
    See application file for complete search history.

(56) References Cited

U.S. PATENT DOCUMENTS

| | | | | |
|---|---|---|---|---|
| 5,493,593 | A * | 2/1996 | Muller et al. ................. | 378/19 |
| 5,708,691 | A | 1/1998 | Zmora | |
| 5,825,842 | A | 10/1998 | Taguchi | |
| 6,301,325 | B1 * | 10/2001 | Besson et al. ................ | 378/15 |
| 6,415,012 | B1 * | 7/2002 | Taguchi et al. ............... | 378/15 |
| 6,490,334 | B1 * | 12/2002 | Wang et al. .................. | 378/15 |
| 6,751,283 | B1 * | 6/2004 | van de Haar ................ | 378/17 |

FOREIGN PATENT DOCUMENTS

| | | |
|---|---|---|
| JP | 5-317302 | 12/1993 |
| JP | 8-187240 | 7/1996 |

OTHER PUBLICATIONS

L. Spies, et al., Physics in Medicine and Biology, vol. 46, No. 3, pp. 821-833, XP-002266217, "Correction of Scatter in Megavoltage Cone-Bean CT", Mar. 2001.

S. Schaller, et al., "Exact Radon Rebinning Algorithm for the Long Object Problem in Helical Cone-Beam CT", IEEE Trans. Med. Ing. 19, 2000, 1 page (Abstract only).

Marc Kachelriess, et al., "Advanced Single-Slice Rebinning in Cone-Beam Spiral CT", Med Phys., vol. 27, No. 4, Apr. 2000, pp. 754-772.

* cited by examiner

Primary Examiner—David V Bruce
(74) Attorney, Agent, or Firm—Oblon, Spivak, McClelland, Maier & Neustadt, P.C.

(57) ABSTRACT

A computed tomography apparatus includes a two-dimensional data acquisition system which acquires projection data of a radiographic region within a subject using a multirow detector, and a hybrid image reconstruction system which reconstructs an image of the radiographic region on the basis of both the projection data and additional data calculated from the projection data. The hybrid image reconstruction system functionally includes a unit for calculating an additional intermediate beam data set, a unit for executing hybrid reconstruction of an oblique section, and a unit for generating a parallel section group. Owing to the construction, there are provided an image reconstruction method which is practicable and which affords a high precision, and a three-dimensional CT system which has the functions of the image reconstruction method.

22 Claims, 20 Drawing Sheets

PARALLEL DATA GROUPS BASED ON CONE-PARALLEL CONVERSION

USING ALL DATA (-60°- 60°)
USING SOME OF DATA (-80°- -60°, 60°- 80°)

PART WHERE DATA ARE DIRECTLY USED WITHOUT CP CONVERSION

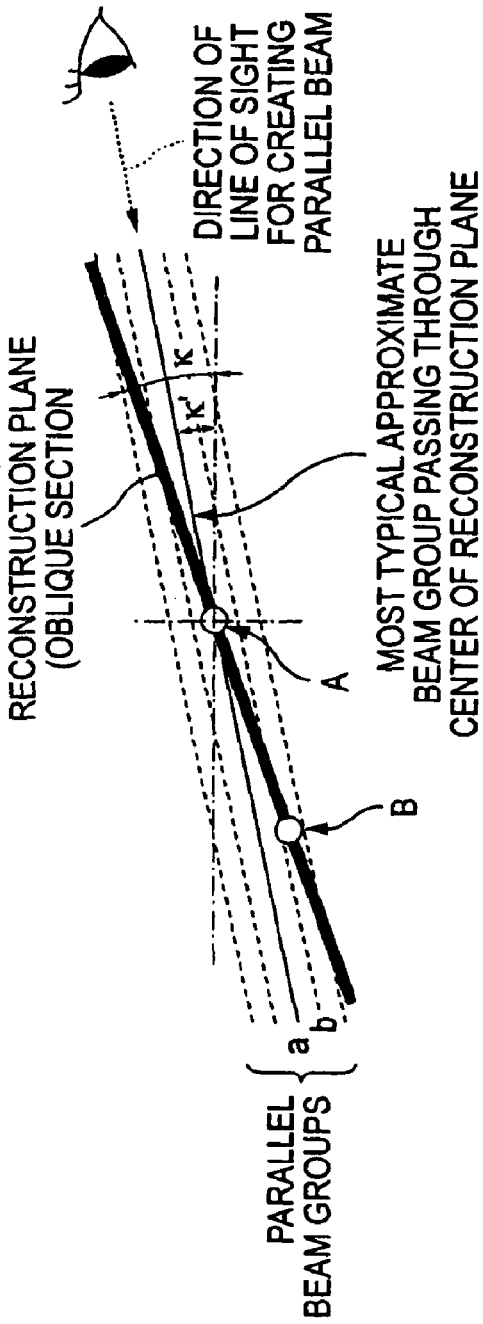
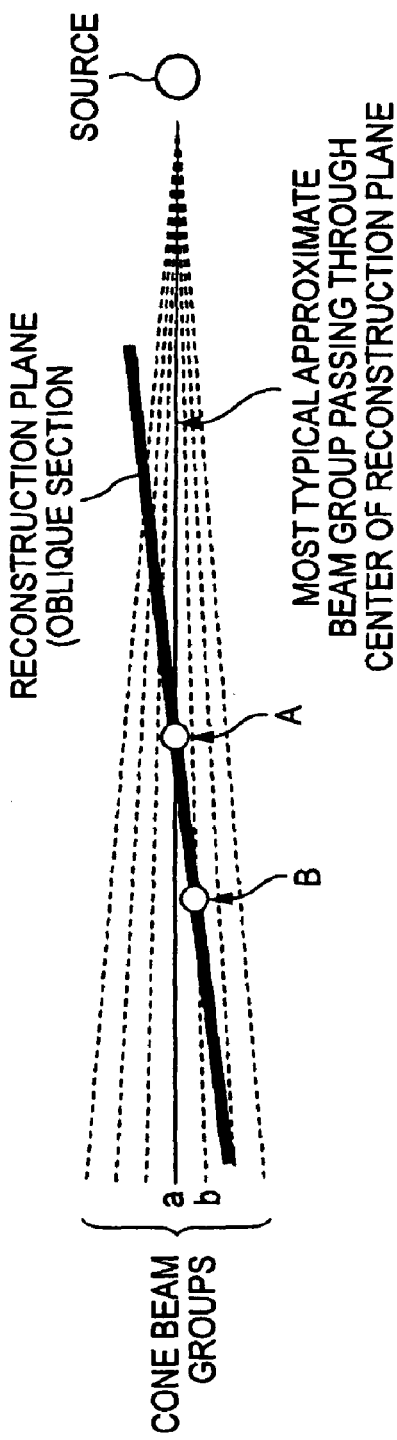
FIG. 19A
FIG. 19B

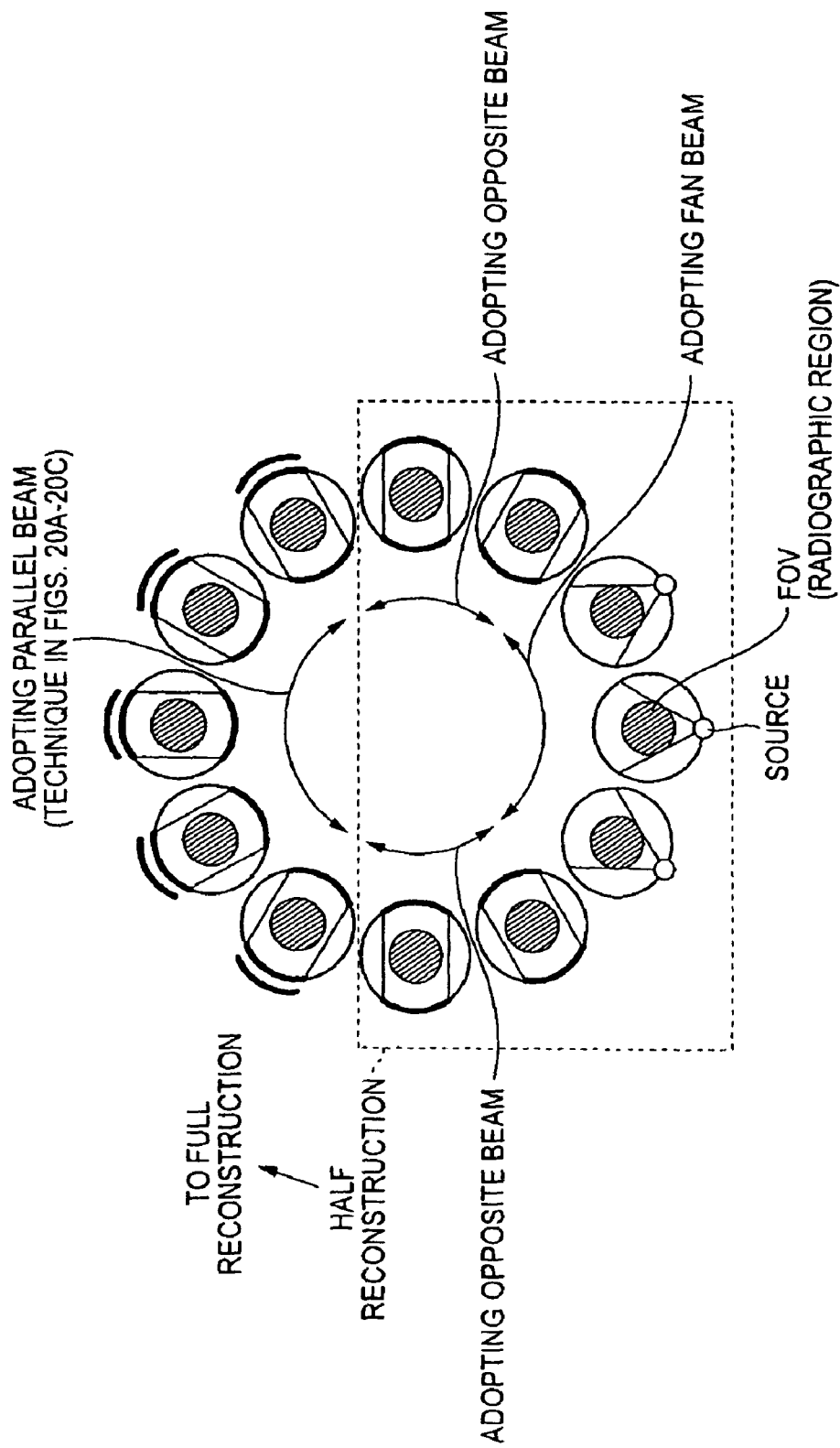

COMPUTED TOMOGRAPHY APPARATUS AND PROGRAM

BACKGROUND OF THE INVENTION

1. Field of the Invention

The present invention relates to a computed tomography ("CT") apparatus, and more particularly to the image reconstruction method of cone-beam helical CT wherein an X-ray source has a helical trajectory.

2. Description of the Related Art

In recent years, in the field of X-ray CT, basic image reconstruction algorithms have been continuously developed and variously proposed for the practicability of three-dimensional (3D) image display. In, for example, so-called "cone-beam helical CT" wherein an X-ray source has a helical trajectory, a large number of approximate reconstruction techniques have been proposed. The techniques include what is called "TCOT (True COne beam Tomography reconstruction algorithm) method", a helical oblique section reconstruction method (also called "ASSR method"), etc. These reconstruction techniques obtain approximate solutions to the last, but the existence of an exact solution has recently been demonstrated in the cone-beam helical CT.

The researches and developments, feasibilities, etc. of the image reconstruction algorithms of the CT will be outlined in the order of (1) helical CT, (2) multi-slice helical CT based on fan-beam geometry, (3) a scheme for obtaining an approximate solution in 3D helical CT based on cone-beam geometry, and (4) a scheme for obtaining an exact solution in the 3D helical CT based on the cone-beam geometry.

(1) Helical CT

In helical CT, a diagnostic table is moved in synchronism with the rotation of an X-ray source (source) as well as a detector, whereby the X-ray source is caused to depict a helical motion relatively to a subject or patient, virtual projection data corresponding to any slice positions designated between adjacent helices are created in succession usually by linear interpolations, and the image of the subject is reconstructed on the basis of the virtual projection data. In effect, however, only one slice is substantially obtained per revolution. By way of example, if 2 mm-slice data are to be created for a region which has a thickness corresponding to 100 mm, radiographing operations of 50 revolutions are required.

(2) Multi-Slice Helical CT Based on Fan-Beam Geometry

As the expansion of the helical CT, there has been known multi-slice helical CT based on a scheme wherein a detector is constructed in the form of 2–4 channels in a slicing direction. According to the multi-slice helical CT, a data acquisition rate becomes 2–4 times as high as in the ordinary helical CT.

In practical use, with the detector having 4 channels or so in the slicing direction, it has been verified that, even when individual projection data obtained by the different channels are regarded as parallel beams which are parallel to the slicing direction, namely, multilayer two-dimensional fan beams which are based on fan-beam geometry, they are little problematic in the reconstruction thereof. Such a scheme has already been put into practical use.

(3) Scheme for Obtaining Approximate Solution in 3D Helical CT Based on Cone-Beam Geometry When the number of channels of the detector in the multi-slice helical CT is further increased from 2–4 to 8 or 16, individual projection data obtained by the different channels can no longer be regarded as the parallel beams based on the fan-beam geometry, and cone-beam geometry needs to be considered.

A first solution based on the cone-beam geometry in this case is a helical oblique section reconstruction method proposed in JP-A-8-187240 by the inventor. Also, a technique called "ASSR method" (Kachelriess: Med. Phys., 27, 754–772) is substantially equivalent to the helical oblique section reconstruction method.

Besides, what is called "TCOT method" has been proposed (refer to U.S. Pat. No. 5,825,842) as a method wherein a Feldkamp method which is originally a reconstruction technique in the case where a source has a circular trajectory is applied to helical scan.

Any of these techniques is an approximation technique, and artifacts become conspicuous especially in a case where the number of channels in the slicing direction further increases from 8–16 to 32, 64, . . . . It has therefore been required to attain a still higher precision.

(4) Scheme for Obtaining Exact Solution in 3D Helical CT Based on Cone-beam Geometry On the other hand, it has been demonstrated in recent years that, in a case where a source has a trajectory such as helical trajectory, an exact solution is theoretically existent even for a long and large object and even in a smooth functional system. Regarding the existence of the exact solution, some demonstrations have been given as stated in, for example, Schaller et al.: "Exact Radon rebinning algorithm for long object problem in helicalcone-beamCT", IEEE Trans. Med. Imag. 19361–75 (2000).

Approaches to the developments of image reconstruction algorithms having heretofore been made, however, have had the problem that, although the exact solution is concerned, the quantity of computations is large, so degradation ascribable to interpolation processing is liable to occur in case of employing actual discrete data. There has also been the problem that, since the range of data necessary for obtaining a certain slice image is wide, the data are easily influenced by the peripheral tissues of a subject and the temporal fluctuation thereof, so they are not satisfactory for use in a medical image diagnostic equipment.

Therefore, further improvement is desired. In particular, in three-dimensional CT whose practical use has been started at present, especially in 3D helical CT based on cone-beam geometry, it is desired to develop a new practicable technique which employs only data having a still higher precision and being necessary and sufficient to the utmost. Nevertheless, it is an actual situation that the precisions of approximations by techniques hitherto proposed cannot be said satisfactory, and that artifacts remain yet.

SUMMARY OF THE INVENTION

The present invention has been made in view of such circumstances of the prior art, and has for its object to provide an image reconstruction method which is practicable and affords a high precision, as well as a three-dimensional CT system which has the functions of the image reconstruction method.

The present invention consists in proposing a new image reconstruction algorithm in three-dimensional (3D) CT. The new image reconstruction algorithm is easily understood when concretely considered as an algorithm which enhances the approximation precision of the prior-art method "Helical oblique section reconstruction method" (refer to JP-A-8-187240). That is, it is a new reconstruction method for a helical oblique section as combines the cone beam data set of a helical trajectory actually acquired, and a parallel beam data set which is theoretically existent as an exact solution and which is partially generated.

More generally speaking, the reconstruction method is such that the partial or intermediate data set of a beam group being theoretically existent is calculated in addition to the cone beam data set actually acquired, whereupon the data sets are used in combination.

Typically, the reconstruction method is a method in which, when a certain reconstruction plane is supposed, an approximate data set necessary for executing two-dimensional reconstruction is picked out from the two data sets. The necessary data set may consist entirely of parallel beam data, or it may well be composed by combining parallel beam data and fan beam data. Further, the precision of reconstruction may well be enhanced by setting beams thought to be optimal, at each individual point as in the Feldkamp method or TCOT method being the prior-art methods.

The present invention has introduced the new idea of synthesizing a plurality of sorts of data, and there are new secondary techniques in this connection. One of the techniques is CT having an oblique section reconstruction function, in which a fan beam or a parallel beam that includes a beam passing through each point of a reconstruction plane is used every point. The other technique is CT which is characterized in that a two-dimensional reconstruction image is generated using both fan beam data and parallel beam data.

As described above, according to the present invention, it is possible to provide an image reconstruction method which is practicable and affords a high precision, and also a three-dimensional CT system which has the functions of the image reconstruction method. More specifically, in a helical oblique section reconstruction method in helical CT having a multirow detector, an image can be obtained with a higher approximation precision than in the prior-art method, and a three-dimensional image can be acquired at high speed and with fewer artifacts than in the prior-art method. Thus, the secondary advantages are expected to be brought forth that the resolution and definition of a three-dimensional CT image are enhanced, and that the distortion of the signal value of the CT image becomes small.

The concrete construction and features of the present invention will be clarifed from the ensuing embodiments thereof when read in conjunction with the accompanying drawings.

BRIEF DESCRIPTION OF THE DRAWINGS

FIG. 2A is a block diagram showing the schematic layout of the whole CT apparatus according to an embodiment of the present invention, while

FIGS. 7A–7C are diagrams for explaining a parallel beam creation domain, wherein FIG. 7A is a diagram showing the locus of a source and a cone-parallel conversion domain as seen in the direction of the line of sight, FIG. 7B is a diagram with the locus of the source seen from above, and FIG. 7C is a diagram with the cone-parallel conversion domain observed from below;

FIG. 10A is a processing flow chart showing all the processing steps of hybrid reconstruction, while

FIG. 12A is a diagram plotting a situation where a source is moved at intervals of 5 degrees along a source trajectory as viewed in the direction of the line of sight, in the case of a first embodiment (κ=10.5 degrees, κ'=9.5 degrees), while

FIG. 14A is a diagram showing the generatable range of parallel beams and approximate data in the case of the first embodiment (κ=10.5 degrees, κ'=9.5 degrees), while

FIG. 17A is a diagram showing the generatable range of parallel beams and approximate data in the case of a second embodiment (κ=10.5 degrees, κ'=9.5 degrees, κ"=8 degrees), while

FIGS. 19A and 19B are diagrams for explaining a case where a technique equivalent to the TCOT method is conjointly applied to the present invention, wherein FIG. 19A is a diagram for explaining parallel beam groups, while FIG. 19B is a diagram for explaining cone beam groups;

FIG. 21 is a diagram for explaining an example in which the present invention is expanded to the full reconstruction.

DETAILED DESCRIPTION OF THE PREFERRED EMBODIMENTS

Now, embodiments of a computed tomography apparatus according to the present invention will be described with reference to the accompanying drawings.

A new reconstruction method in cone-beam CT as proposed here is such that two approaches hitherto known are organically combined. In the ensuing description, therefore, the reconstruction method of the cone-beam CT according to the present invention shall be called "hybrid reconstruction method" on occasion. Especially, a case where the "hybrid reconstruction method" is applied to a helical oblique section reconstruction method being a typical example of incarnation shall be called "helical-oblique-section hybrid reconstruction method" on occasion in the ensuing description.

Figure 1:
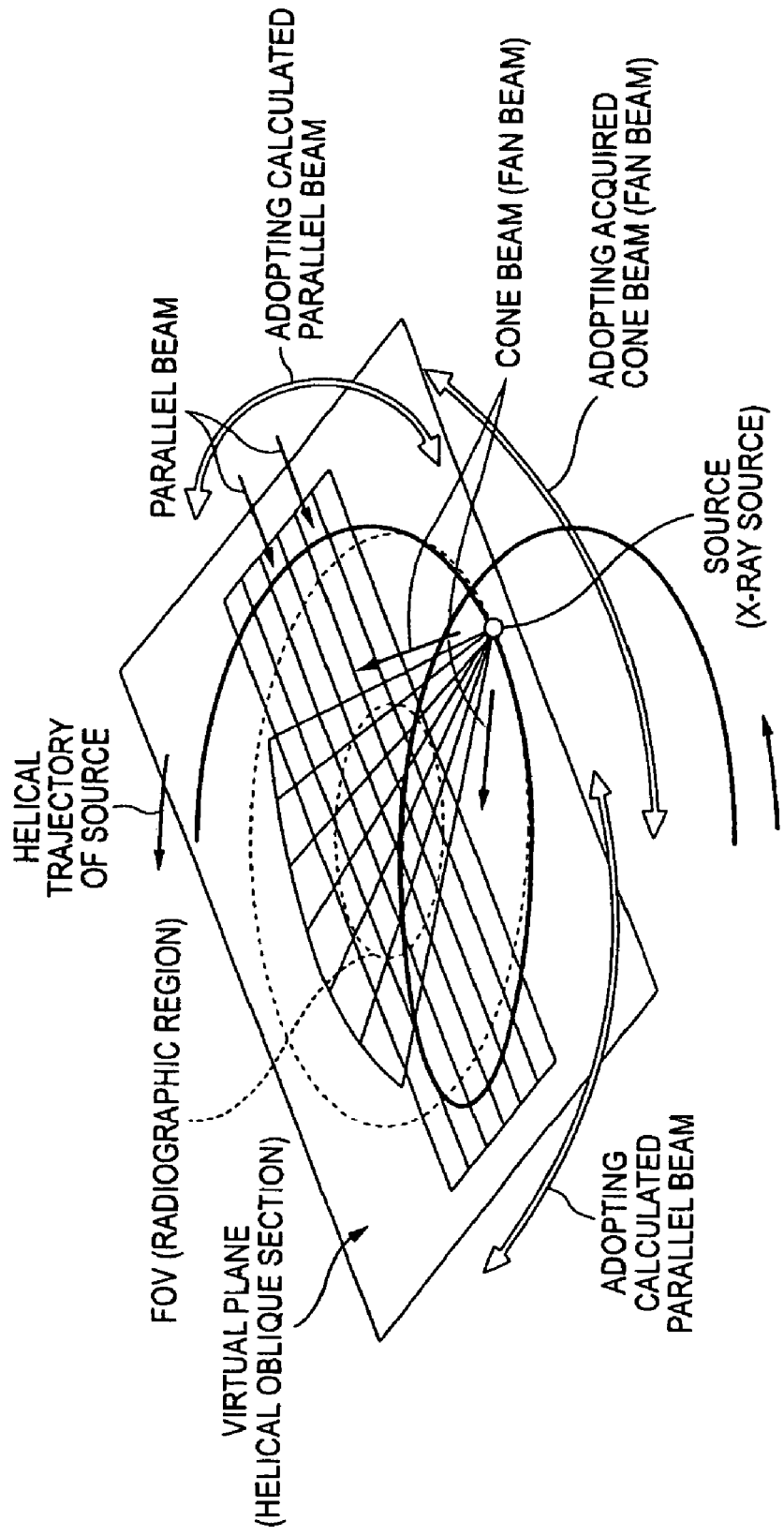
FIG. 1 is a diagram showing the fundamental concept of hybrid reconstruction in an embodiment of the present invention.

FIG. 1 serves to explain the fundamental concept of the helical-oblique-section hybrid reconstruction method. As shown in FIG. 1, the helical-oblique-section hybrid reconstruction method employs for original beam data for use in the reconstruction thereof, both a group of acquired beams at a part of good approximation precision in approximate projection beams (cone beams, fan beams) in the helical oblique section reconstruction method, and groups of parallel beams calculated at only necessary localized parts in a group of parallel beams which can be obtained as an exact solution (to be described later) from the group of acquired beams. The details will be stated later.

(Equipment Layout of CT According to This Embodiment)

Figure 2A:
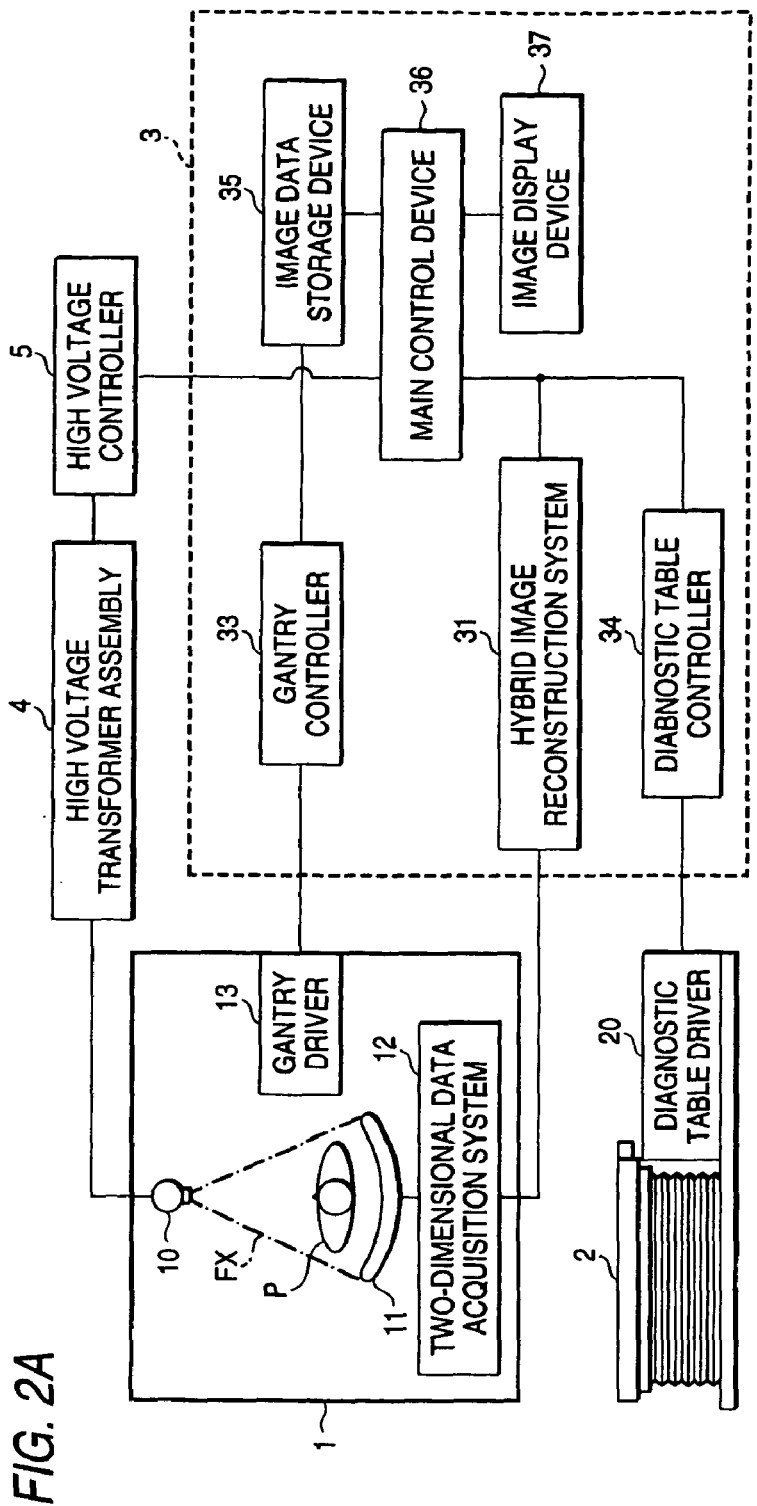
Figure 2B:
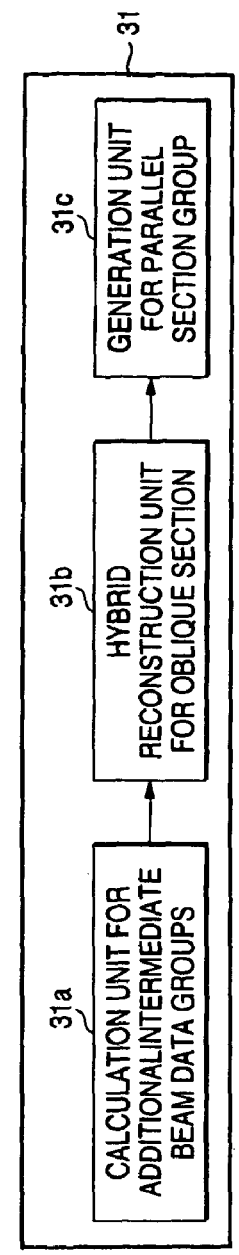
FIG. 2B is a block diagram showing the schematic layout of a hybrid reconstruction system in the CT apparatus.
Figure 3:
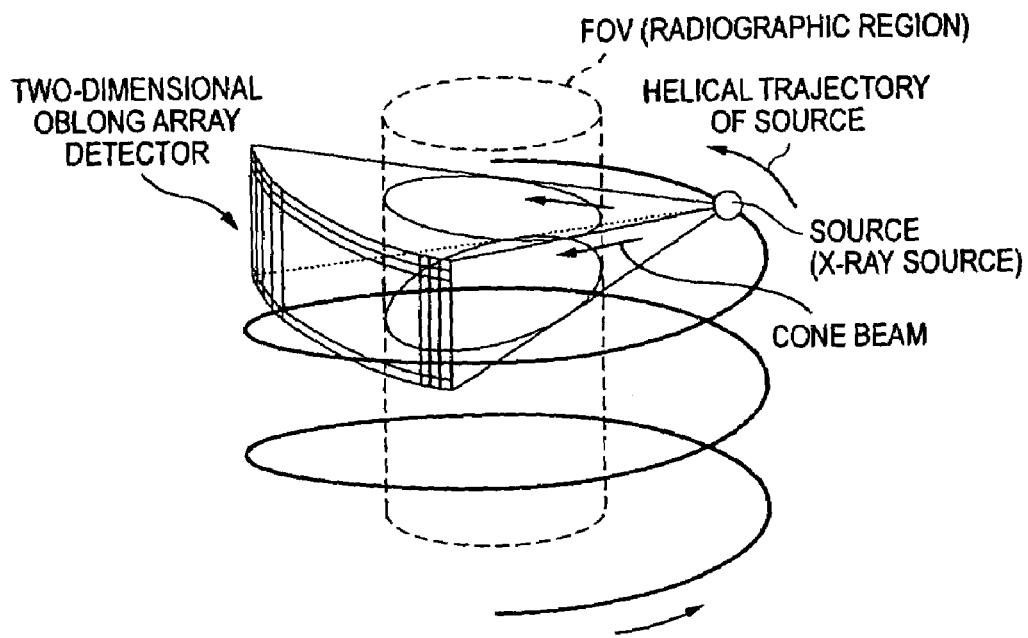
FIG. 3 is a diagram showing the helical trajectory of an X-ray source and the arrangement of a two-dimensional detector in 3D helical scan.

FIGS. 2A and 2B serve to explain the equipment layout of CT which employs the helical-oblique-section hybrid reconstruction method. Applicable as the CT is, for example, one which is similar to the multi-slice helical CT being the foregoing prior-art example. The number of channels in a slicing direction is supposed to be about 16 to several tens, or a somewhat large number of one hundred and several tens. The most typical example is helical CT which has a multirow detector of about 16–64 channels as shown in FIG. 3, but this shall not be an upper limit.

The CT shown in FIGS. 2A and 2B includes a gantry 1, a diagnostic table 2 and a console 3, and it is driven by, for example, an R-R scheme under the general control by a main control device 36 which is included in the console 3 and which takes charge of the control center of the whole apparatus. In the example shown in FIG. 2A, the longitudinal direction of the diagnostic table 2 is set as an array direction (rotational axis direction or slicing direction), and two directions orthogonal thereto are respectively defined as a channel direction and a beam irradiation direction.

A tabletop is disposed on the upper surface of the diagnostic table 2 in a state where it is supported so as to be slidable in the longitudinal direction of this diagnostic table, and a subject or patient P is put on the upper surface of the tabletop. The tabletop is retreatably inserted into the diagnostic opening (not shown) of the gantry 1 by driving a diagnostic table driver 20 which is represented by a servomotor. The diagnostic table driver 20 is fed with a drive signal from a diagnostic table controller 34 which is included in the console 3. Besides, the diagnostic table 2 includes a position detector, such as encoder (not shown), which detects the longitudinal position of the tabletop in terms of an electric signal, and the detection signal is sent to the diagnostic table controller 34 as a signal for controlling the diagnostic table.

The gantry 1 has in its interior a rotary frame (not shown) which is substantially cylindrical, and the diagnostic opening mentioned above is located inside the rotary frame as shown in FIG. 2A. Besides, an X-ray tube 10 and a multirow detector 11 being an X-ray detector are disposed in the rotary frame so as to oppose to each other while interposing therebetween the patient P who is inserted in the diagnostic opening located inside the rotary frame. Further, a high voltage transformer assembly 4, a pre-collimator as well as a post-collimator being a scattered-radiation elimination collimator, a two-dimensional data acquisition system 12, and a gantry driver 13 are disposed at the predetermined positions of the rotary frame.

Among them, the X-ray tube 10 functioning as an X-ray source has the structure of, for example, a rotating anode X-ray tube, in which current is continuously caused to flow through a filament from the high voltage transformer assembly 4, thereby to heat the filament and to emit thermions toward a target. The thermions collide against a target face so as to form an effective focal spot, and an X-ray beam is continuously caused to irradiate with a spread from the position of the effective focal spot of the target face.

The high voltage transformer assembly 4 is fed with a low supply voltage from a power source device through a low-voltage slip ring, and with the control signal of the X-ray irradiation from a high voltage controller 5 through an optical signal transmission system. Therefore, the high voltage transformer assembly 4 generates a high-voltage from the fed low supply voltage, and it generates a continuous tube voltage corresponding to the control signal from the high voltage and feeds the tube voltage to the X-ray tube 10.

The pre-collimator is located between the X-ray tube 10 and the patient P, while the scattered-radiation elimination collimator being the post-collimator is located between the patient P and the multirow detector 11. The pre-collimator 22 is formed with an opening of, for example, slit shape as has a predetermined width in, for example, the array direction. Thus, the X-ray beam irradiating from the X-ray tube 10 has its width limited in the array direction, so as to form a cone beam of desired slice width corresponding to, for example, a plurality of detection element arrays in the multirow detector 11.

The X-ray tube 10 and the multirow detector 11 are rotatable in the opposing state around a rotational axis in the axial direction of the diagnostic opening, within the gantry 1 through the rotation of the rotary frame.

Besides, the multirow detector 11 is the detector in which the plurality of arrays of detection elements having a plurality of detection channels are arranged in a slicing direction (refer to FIG. 3). By way of example, the detection portion of each detection element is constructed of a solid-state detector which includes a scintillator and a photodiode for once converting entered X-rays into an optical signal and then converting the optical signal into an electric signal. Besides, each detection element is provided with a charge accumulation portion (sample and hold portion). Therefore, the multirow detector 11 has such a structure that the charge accumulation portions are sequentially selected by a group of switches in the two-dimensional data acquisition system 12 so as to read out charges, thereby to detect signals (projection data) which represent the intensities of transmitted X-rays. Incidentally, a sensor (such as I. I.) of the type which converts entered X-rays directly into an electric signal may well be employed as each detection element.

The two-dimensional data acquisition system 12 has the structure of a so-called "filtered DAS (Data Acquisition System)" in which detection signals are sequentially read out from the individual detection elements of the multirow detector 11 by changing-over the group of switches, so as to perform A/D conversion (to convert the detection signals into voltages and sample the voltages). In order to incarnate such operations, the two-dimensional data acquisition system 12 includes array selection portions in the number of, for example, N channels, considering the fact that the detector is the multirow detector 11, a single channel selection portion, a single A/D converter, and a control circuit.

A data transmission portion, not shown, connects signal paths on a rotating side and a fixed side within the gantry 1, and an optical transmission system which transmits signals in non-contact fashion is used here by way of example. Incidentally, the structure of a slip ring may well be employed as the data transmission portion. The projection data of digital quantity derived through the data transmission portion are sent to a hybrid image reconstruction system 31 to be described later as is included in the console 3.

Further, the gantry driver 13 includes a motor which rotates all the rotating side elements in the gantry 1, together with the rotary frame, around its axis, and it also includes a gear mechanism, etc. The gantry driver 13 is fed with a drive signal from a gantry controller 33.

The high voltage controller 5, diagnostic table controller 34 and gantry controller 33 are interposed between the gantry 1 and diagnostic table 2 and the console 3 signal-wise, and they drive the load elements in charge, in response to control signals from the main control device 36.

In addition to the main control device 36 which controls the whole system, the console 3 includes the gantry controller 33, the diagnostic table controller 34, the hybrid image reconstruction system 31, an image data storage device 35, and an image display device 37 which are connected to the main control device 36 through buses. Besides, a correction unit, an input unit, etc., not shown, are included.

In compliance with a processing command from the main control device 36, the correction unit (not shown) subjects the projection data of digital quantity sent from the two-dimensional data acquisition system 12, to various correction processes such as offset correction and calibration correction. The acquired data subjected to the correction processes are once stored and saved in the image data storage device 35 in compliance with a write command from the main control device 36. The saved data are read out from the image data storage device 35 and then transferred to the hybrid image reconstruction system 31 in compliance with a read command which is issued at a desired timing by the main control device 36.

As shown in FIG. 2B, the hybrid image reconstruction system 31 functionally includes a calculation unit 31a for additional intermediate beam data sets, a hybrid reconstruction unit 31b for an oblique section, and a generation unit 31c for a parallel section group. The system 31 executes a reconstruction process (to be described later) based on a three-dimensional reconstruction algorithm being the principle of the present invention, through the processes of the respective units 31a–31c, under the control of the main control device 36 and at a stage where the acquired data for reconstruction have been transferred. Thus, it generates the image data of a three-dimensional region. Under the control of the main control device 36, the image data are saved in the image data storage device 35 and are sent to the image display device 37 as may be needed.

The image display device 37 subjects the image data to necessary processes such as a coloration process and a superposition process for annotation data or scan information, and it subjects the resulting image data to D/A conversion so as to display them as a CT image.

The input unit (not shown) is used for giving the main control device 36 instructions for scan conditions (including a part and a position to be scanned, the thickness of a slice, the voltage and current of the X-ray tube, the direction of scanning the patient, etc.), image display conditions, and so forth.

Incidentally, the X-ray tube 10, multirow detector 11 and two-dimensional data acquisition system 12 in this embodiment constitute data acquisition means according to the present invention, and the hybrid image reconstruction system 31 constructs image reconstruction means.

Here, the principle of the hybrid image reconstruction method forming the skeleton of this embodiment will be described in conjunction with FIG. 4–FIG. 11.

(Image Reconstruction)

Figure 4:
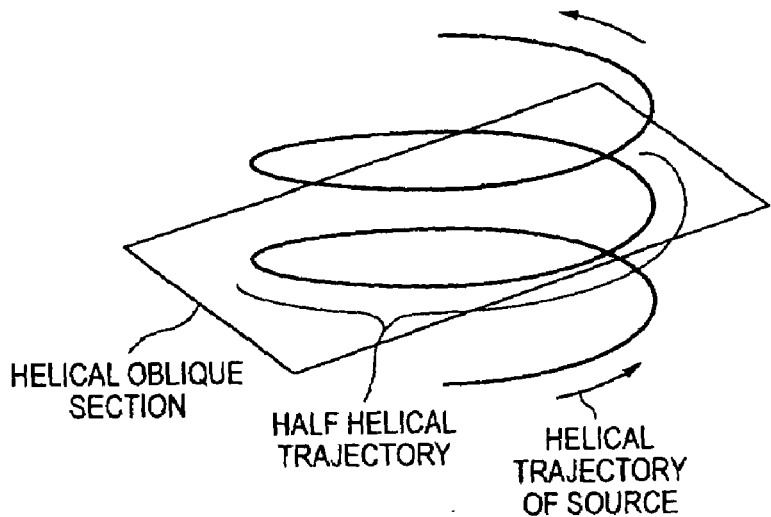
FIG. 4 is a diagram showing a half helical trajectory and a helical oblique section.

FIG. 4 serves to explain the basic idea of the prior-art method "helical oblique section reconstruction method" (refer to JP-A-8-187240). With note taken of the fact that, as shown in FIG. 4, the half revolution or so of the helical trajectory of an X-ray source (source) is approximately contained in one plane, projection data (beam data) near the oblique plane "helical oblique section" are picked out and collected so as to execute ordinary two-dimensional half reconstruction. A method called "ASSR method" (Kachelriess: Med. Phys., 27, 754–772) is also known as a prior-art technique which is substantially equivalent to the method shown in FIG. 4.

In the present invention, acquired data are directly adopted for reconstruction at a part which touches the oblique section, but parallel beams the generatability of which has been demonstrated in IEEE Trans. Med. Imag. 19 361–75 (2000) by Schaller et al. are adopted at both those endparts of the oblique section at which the grades of approximations worsen (refer to FIG. 1).

Figure 5:
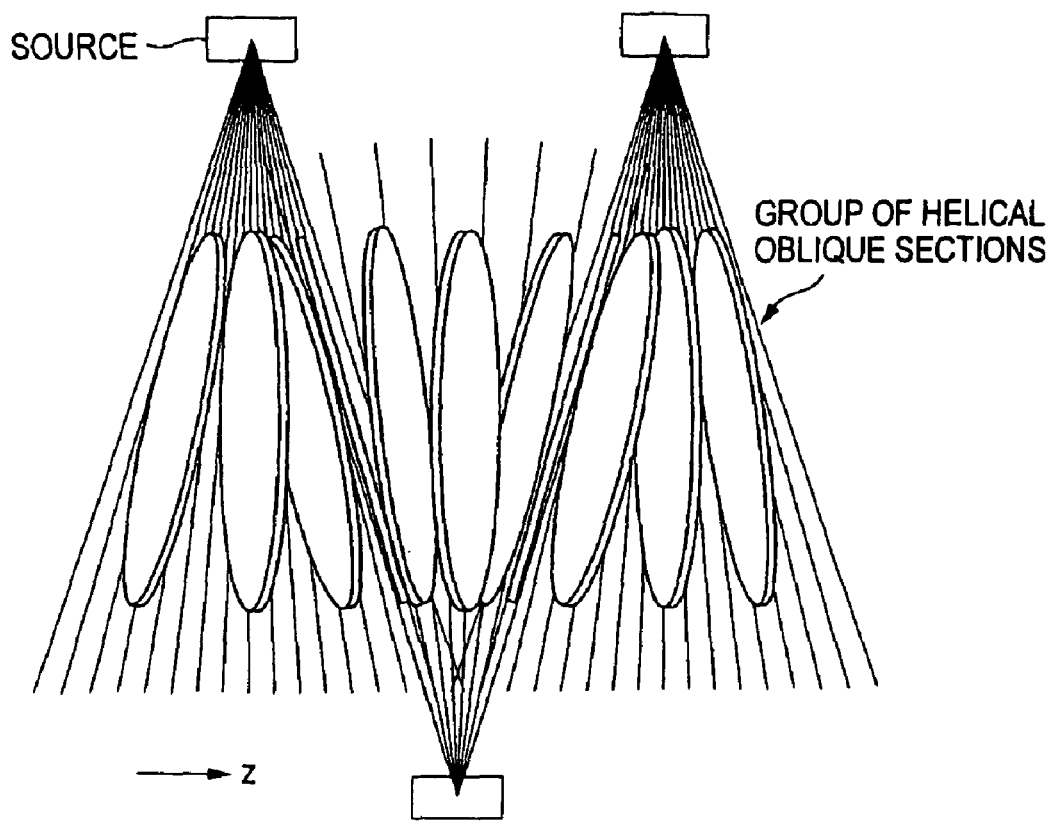
FIG. 5 is a diagram showing groups of oblique sections which are continuously reconstructed.

Although the generation of the parallel beams will be stated later, parallel beam data can be theoretically obtained as an exact solution as to a smooth functional system. In the present invention, the acquired data and the parallel beam data are effectively synthesized, there by to create an oblique section image of high precision. Further, in a case where three-dimensional volumed at a are to be acquired, reconstructing operations may be successively performed while the oblique section is being shifted little by little along the helix of the source, on the basis of the same idea as in the prior-art oblique section reconstruction method, as shown in FIG. 5. Thus, a series of helical oblique section image groups which are not parallel to one another are obtained, and they become the volume data as a whole. The image reconstruction is as outlined above.

(Definition of Terms: Elucidation of Concepts)

Here, terms for use in this specification will be defined. In the ensuing description, four concepts; (1) acquired cone beam data, (2) converted parallel beam data, (3) virtual data, and (4) approximate data will be discriminately considered. They are respectively defined as follows:

(1) Acquired Cone Beam Data

In this specification, the term "acquired cone beam data" will be used in the significance of actually existing projection beams/projection data which have been obtained by actual data acquisition. The acquired cone beam data will be simply termed "projection beams/projection data", or especially when to clarify discrimination, they will be termed, e.g., "projection data actually acquired" without shortening the expression. The set of data are cone beam data every view. They become fan beam data when a partial set contained in a two-dimensional plane is taken out.

(2) Converted Parallel Beam Data

In this specification, the term "converted parallel beam data" will be used in the significance of a partial parallel beam data set which has been generated by computations from the partial set of acquired data. The converted parallel beam data are exact solution in a smooth functional system in a theoretical sense. Since the generation can be also said to be conversion for generating parallel beam data from cone beam data, it shall be called "cone-parallel conversion" or shortly "CP conversion" herein.

(3) Virtual Data

In this specification, the term "virtual data" will be used as virtually supposed items such as a plane supposed for image creation, like the helical oblique section stated before, or beams contained in the plane, and projection data corresponding to the beams. By prefixing "virtual" in this manner, a plane shall be termed "virtual plane", a flat surface "virtual flat surface", a beam "virtual beam", projection data "virtual projection data", and the likes.

By way of example, the expression "virtual projection data" signifies ideal projection data which are required for reconstructing the image of a reconstruction plane (defined as an oblique section here), that is, which lie on an X-ray path (called "virtual path") contained in the reconstruction plane. In helical scan, such virtual projection data do not actually exist but some exceptions.

(4) Approximate Data

The virtual data (3) are not actually existent (in most cases). In this specification, approximate data which substitute for the virtual data are created from the acquired data (1) and the generated data (2) by interpolations, etc. The created data shall be called, e.g., "approximate projection beams/data".

Byway of example, the expression "approximate projection data" signifies projection data lying on that X-ray path (approximate path) in an X-ray beam FX which is the most approximate to the virtual path. Incidentally, the approximate projection data can actually exist as actually existent projection data in some cases, and they cannot actually exist in the other cases. When the approximate projection data do not actually exist, they are created from actually existent projection data near the approximate path by interpolations (distance interpolations). Each of the approximate projection data is created every radiating direction (defined as an angle within a fan) of X-rays from the X-ray source 10, as to each angle of rotation of the X-ray source 10.

(Flow of Processes of Hybrid Reconstruction Method)

The radius of the trajectory of an X-ray source is, for example, about 600 mm, and the helical pitch thereof may be considered about 40–50 mm for a 1 mm-slice and 64 arrays though it depends also upon the number of arrays. Subject to a 2 mm-slice and 64 arrays, the pitch also doubles. Since such quantities change in accordance with settings, values calculated in such a way that the radius of the trajectory of the X-ray source and the helical pitch are both simplified and normalized to "1 (one)" will be employed in the ensuing description (although the helical pitch is too large, no problem is incurred in the description of the present invention).

I. Setting of Virtual Plane

In the prior-art method "helical oblique section reconstruction", a virtual plane is set so that errors from the partial set ("half helix") of the helical trajectory of a source as corresponds to view data for 180 degrees+a fan angle (denoted by 2A, and being about 50 degrees typically) required for half reconstruction may become as small as possible as a whole. The tilt angle of the oblique section is, for example, 15.3 degrees in the normalized definition. The present invention adopts a similar approach, but a virtual plane may well be brought nearer to the tangential direction of a source trajectory because of the addition of converted parallel beam data.

As the example of setting the virtual plane, an example in which an oblique section is brought into agreement with a tangential line will be explained with reference to FIG. 6. An oblique section angle $\kappa$ is $\kappa = \arctan(1/2\pi)$ which is about 9.04°. As will be described later, the setting of this oblique section is not an example favorable for implementation, but it will be first described for the sake of convenience. The example favorable for implementation will be explained after the thorough description of processing.

II. Generation of Converted Parallel Beam Data

Figure 6:
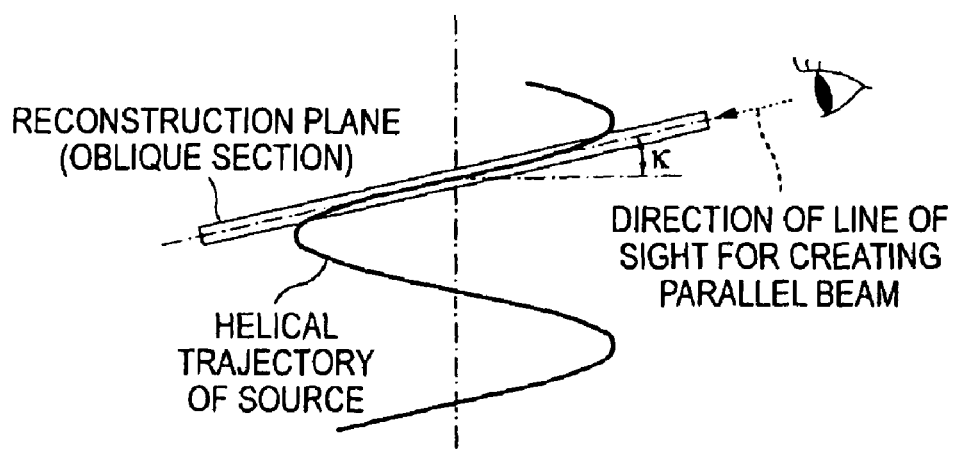
FIG. 6 is a diagram for explaining the direction of the line of sight for creating a parallel beam.
Figure 7A:
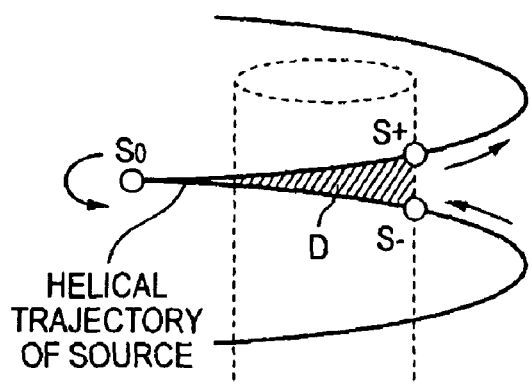

FIG. 7A shows the locus of the source in a direction rotated by 90 degrees from the direction in which the tangential line has been determined in the setting of the virtual plane in FIG. 6, that is, in the direction of the line of sight in FIG. 6. For reference, the locus of the source as seen from above is shown in FIG. 7B.

In FIG. 7A, the locus is in a shape which has an edge like the Greek letter y thrown down sideways. On this occasion, a hatched domain, that is, a two-dimensional pseudo closed domain D which is surrounded with the trajectory of the source is a domain which can be subjected to cone-parallel conversion (CP conversion) (Schaller et al., IEEE Trans. Med. Imag. 19 361–75 (2000)). The projection data of individual beams orthogonal to the sheet of the drawing can be (exactly) calculated within the closed domain D shown in FIG. 7A.

Figure 7B:
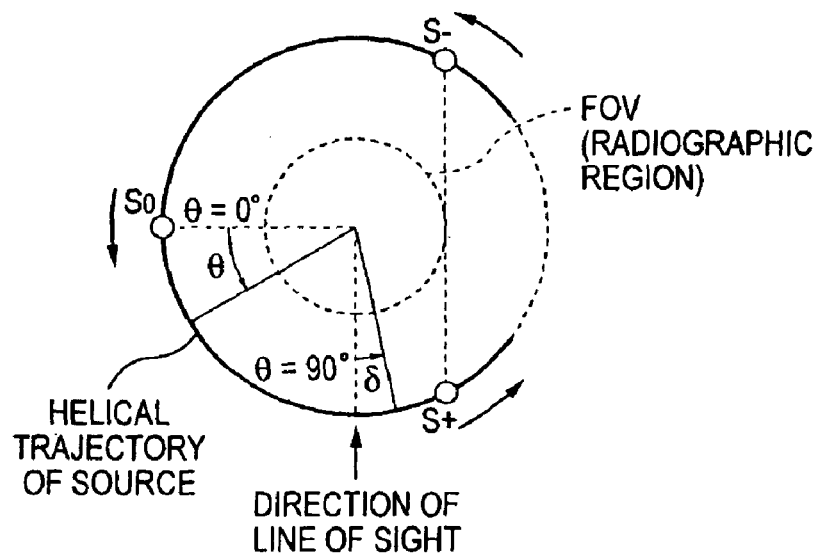
Figure 7C:
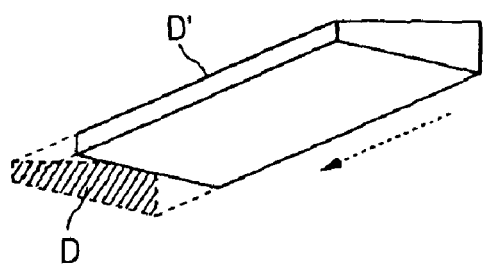

FIG. 7C shows the CP conversion domain observed from below by changing the line of sight. In FIG. 7C, a three-dimensional domain obtained by extending the pseudo closed domain D in an orthogonal direction is denoted by D'.

The locus of the source trajectory corresponding to data used in the CP conversion is a part which is symmetric to a source position $S_o$ at which the oblique section has been determined, and it corresponds to the rotation of "180 degrees+a fan angle" as a whole (refer to FIG. 7B). In the CP conversion, information items from around the potions $S_o$ are also reflected, but the information items of parts which just correspond to opposite beams are chiefly used.

Anyway, it is appreciated that, in the direction of $\theta = 90$ degrees rotated by 90 degrees from the position at which the oblique section has been determined (the corresponding direction is set at $\theta = 0$ degree), the information of a parallel beam which agrees with a virtual beam necessary for the oblique section image reconstruction can be obtained by the CP conversion.

Here, the cone-parallel conversion (CP conversion) will be supplemented.

Since the CP conversion is a known technique (for example, Schaller et al., IEEE Trans. Med. Imag. 19 361–75 (2000)), it shall not be described in detail, and it is as outlined below.

Figure 8A:
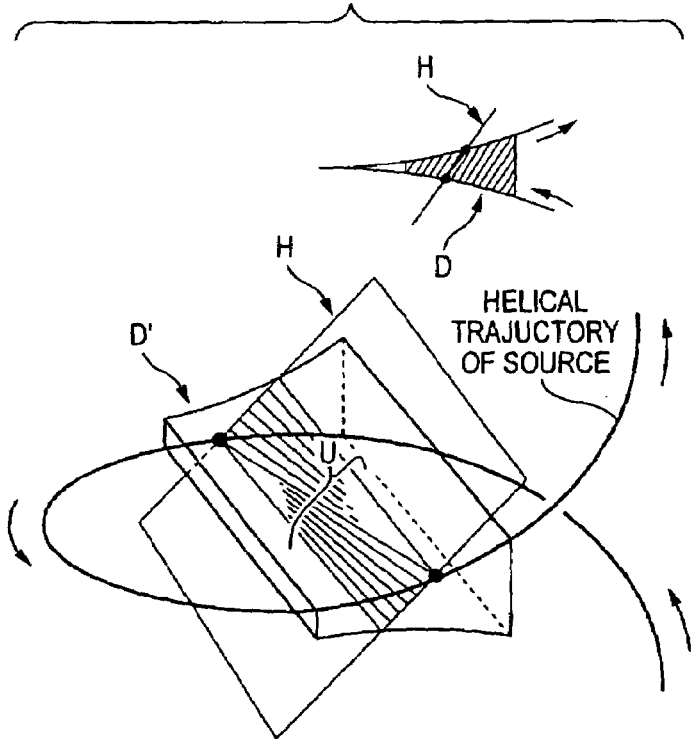
FIGS. 8A–8D are diagrams for explaining cone-parallel conversion for generating a parallel beam from a cone beam.
Figure 8B:
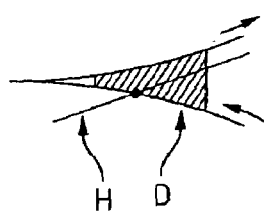
Figure 8C:
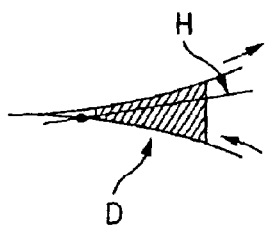
Figure 8D:
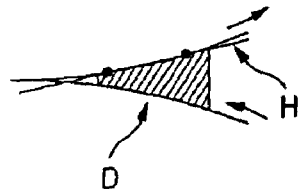

(1) First, the common part between an FOV (radiographic region) contained in the three-dimensional pseudo closed domain D' and a plane H orthogonal to the two-dimensional pseudo closed domain D is expressed as the sum set U of fan beams from a finite number of sources. This example is shown in FIG. 8A. The three-dimensional pseudo closed domain D' and the plane H intersect in several patterns, and the respective patterns are shown in FIGS. 8B–8D.

(2) Subsequently, individual beams in the sum set U are differentiated in a direction perpendicular to the plane H within cones to which the beams belong originally, and the resulting differential values are integrated for the whole set U (the integral value is denoted by $\sigma$). The parallel ones of such planes H orthogonal to the two-dimensional pseudo closed domain D are collected and arrayed, and the integral values $\sigma$ are successively obtained, whereby an area component in $D' \cap H$ is found.

(3) Besides, BP (back projection) calculations are executed on the basis of the area components found for all the planes H orthogonal to the two-dimensional pseudo closed domain D, whereby an image on the domain D (the fluoroscopic image of a patient in the domain D, in other words, the integral value of parallel beams within the domain D') is obtained. Although this methodology is the prior-art technique, the application of the method in such oblique directions, and the reconstruction processing itself including the point that the series of data are generated while the sense of the conversion is being flexibly changed, the point that the hybrid reconstruction is executed, and so forth, is a quite new idea and has been proposed for the first time by the present invention.

III. Hybrid Reconstruction

Figure 9:
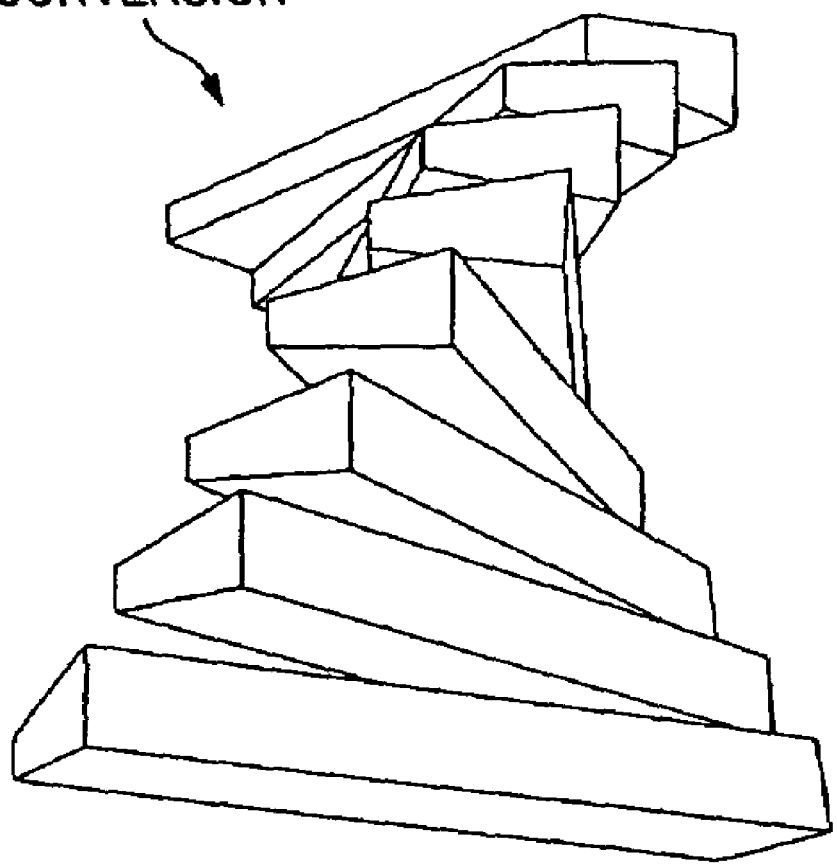
FIG. 9 is a diagram showing a situation where parallel data sets are successively created while the angle of the line of sight is being changed in the cone-parallel conversion.

Meanwhile, parallel data based on such CP conversion can be successively computed while the set position of the oblique section is being changed in the θ direction. The situation is shown in FIG. 9. The pseudo closed domains D' created by changing the angle ought to change the direction while overlapping each other, but the overlaps are lessened in FIG. 9 in order to facilitate understanding.

In this way, in addition to the cone be am data set originally obtained by the acquisition employing the multi-row detector 11, the parallel data sets obtained by the CP conversion can be made candidates for use in the image reconstruction. The processing thus far described is mainly executed by the calculation unit 31a for additional intermediate beam data sets as is included in the hybrid image reconstruction system 31.

Figure 10A:
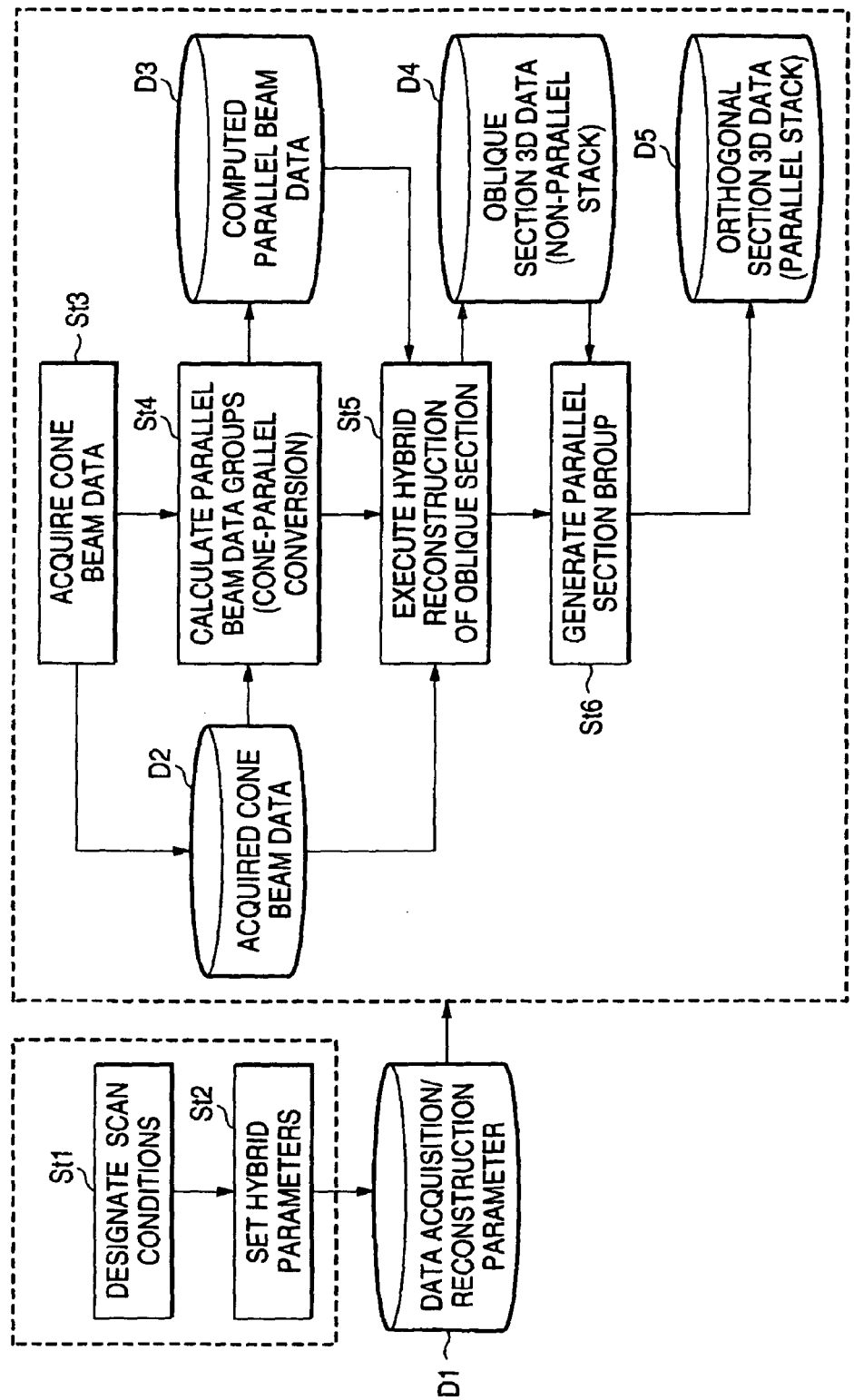
Figure 10B:
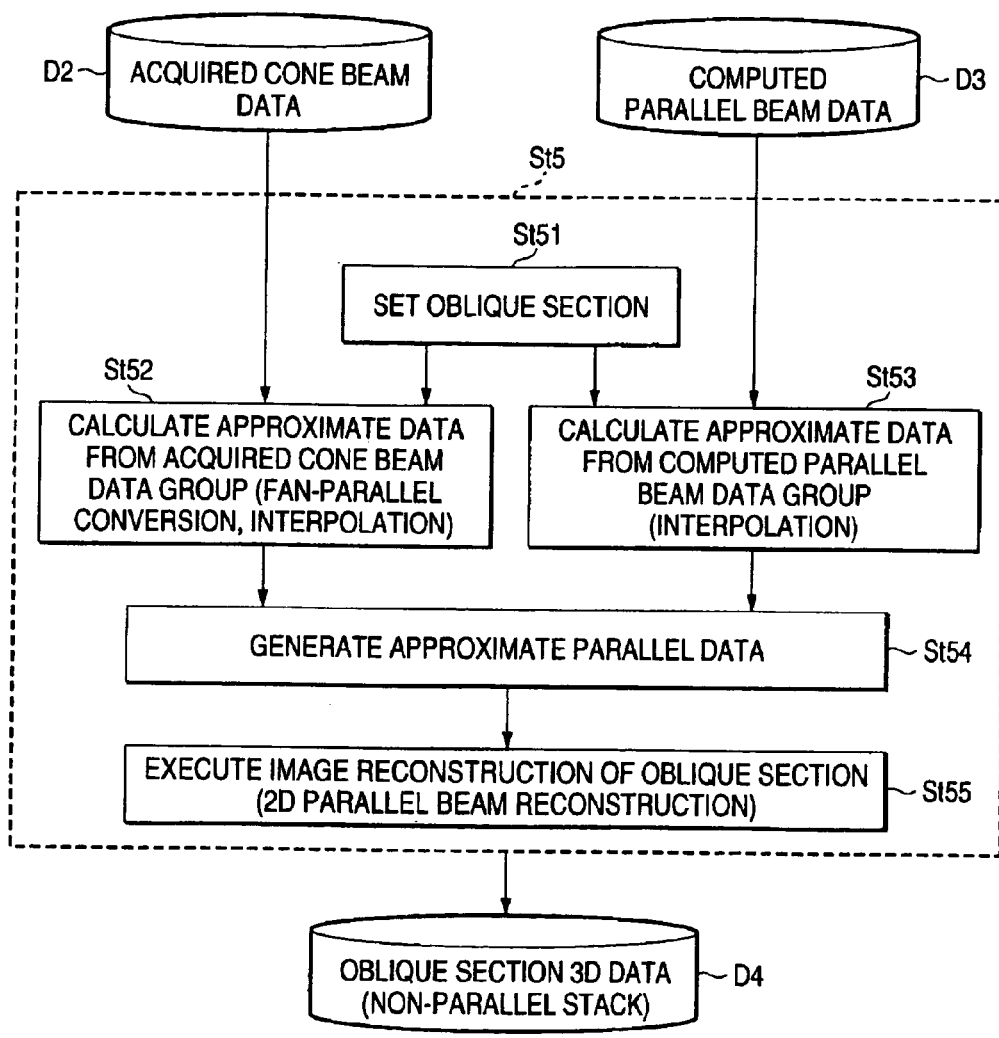
FIG. 10B is a processing flow chart showing the details of the processing steps of the hybrid reconstruction of an oblique section.
Figure 11:
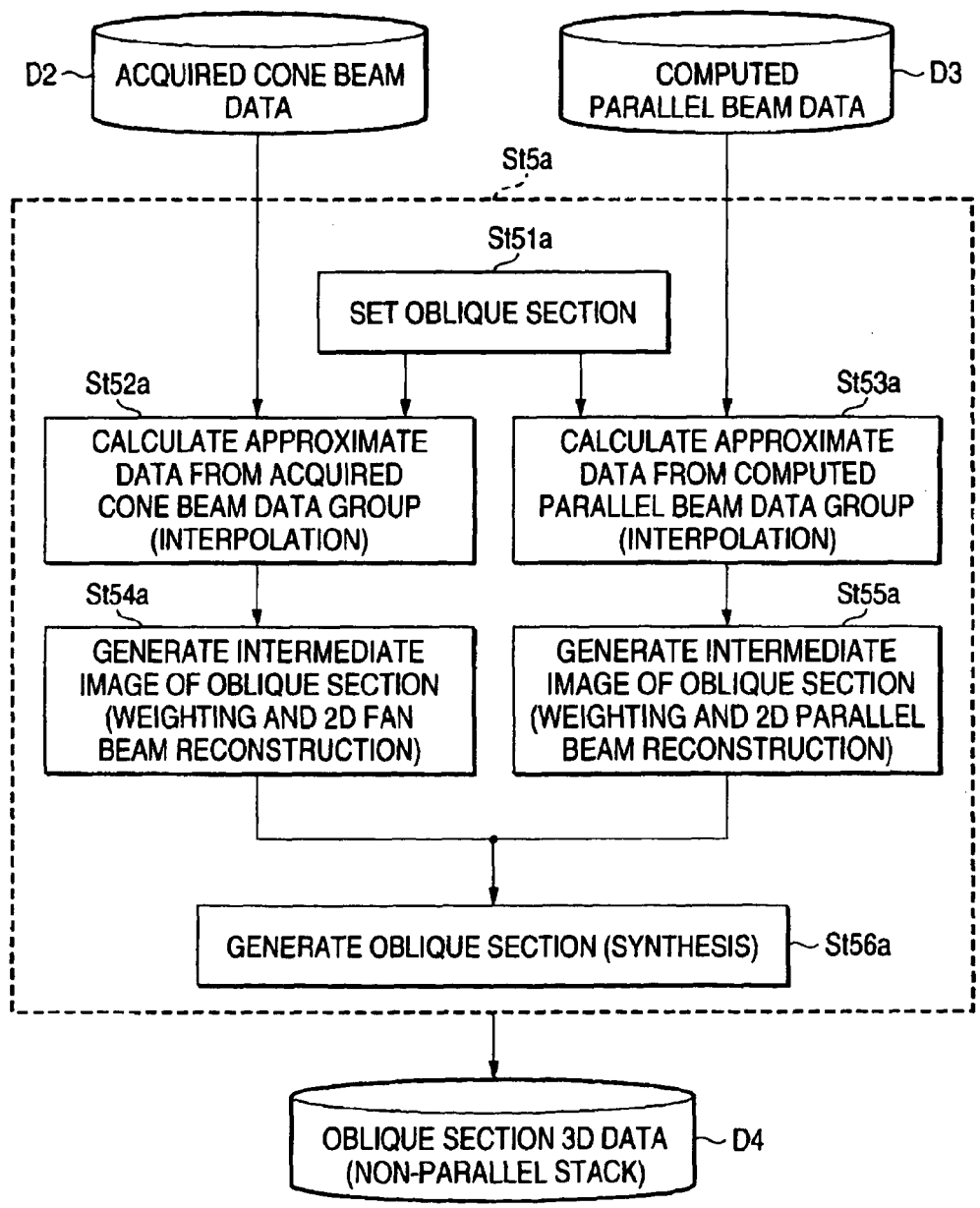
FIG. 11 is a processing flow chart showing a case where fan-parallel conversion is not executed in the hybrid reconstruction process of an oblique section as shown in FIG. 10A.

The flows of the image reconstruction employing the two data sets are shown in FIGS. 10A and 10B and FIG. 11. The general concept is shown in FIG. 1 which is the representative drawing of the present invention.

FIG. 10A is a flow chart showing the processing steps of the whole hybrid reconstruction processing. In accordance with the steps shown in FIG. 10A, first of all, in starting CT scan, scan conditions are set (step St1), hybrid parameters such as κ and κ' and weight functions $w_f$ and $w_p$ to be explained later are set (step St2), and a data acquisition/reconstruction parameter D1 is stored.

Subsequently, the CT scan is performed on the basis of the data acquisition/reconstruction parameter D1 so as to acquire cone beam data (step St3), and the acquired cone beam data D2 are stored. A parallel beam data set is calculated by cone-parallel conversion based on the cone beam data D2 (step St4), and the calculated parallel beam data D3 are stored.

Besides, the process of the hybrid reconstruction of an oblique section is executed on the basis of the acquired cone beam data D2 and computed parallel beam data D3 which are held stored, and mainly in the hybrid reconstruction unit 31b for the oblique section as is included in the hybrid image reconstruction system 31 (step St5), and oblique-section three-dimensional data (non-parallel stack) D4 thus reconstructed are stored. Also, a parallel section group is generated (step St6), and orthogonal-section three-dimensional data (parallel stack) D5 are stored.

FIG. 10B shows the details of the hybrid reconstruction process (step St5) shown in FIG. 10A. Referring to FIGS. 10A and 10B, after the oblique section has been set (step St51), approximate data are respectively calculated from the acquired cone beam data set and the computed parallel beam data set (steps St52, St53), approximate parallel beam data are created using both the approximate data (step St54), and the image reconstruction process for the oblique section is performed with the parallel data properly arranged (step St55).

FIG. 11 shows the details of another processing example (step St5a) of the hybrid reconstruction process (step St5) shown in FIG. 10A. An oblique section is set (step St51a), fan beams are generated as approximate data on the basis of the acquired cone beam data D2 (step St52a), while approximate data are calculated on the basis of the computed parallel beam data D3 obtained by the CP conversion (step St53a), reconstruction planes are reconstructed under suitable weightings separately from each other (steps St54a, St55a), and the resulting two images are lastly synthesized (step St56a). In this case, after the image reconstruction of CT has been subjected to logarithmic transformation, processing is basically linear calculations, and hence, the synthesizing processing may basically be addition processing.

The outline of the flow of the processing is as described above. As stated at the beginning, however, the explanatory example of the oblique section angle $\kappa = \arctan(1/2\pi) \approx 9.04°$ in which the oblique section serving as the virtual plane is held in agreement with the tangential line of the trajectory is not suitable in practical use for the following reasons:

(1) The approximation of the direct acquired data is good only in the close vicinity of the direction (assumed to be θ=0) of the source in which the oblique section has been set, and it worsens greatly at somewhat distant points.

(2) The calculated parallel beams have an exact solution in the direction of θ=90 degrees, but the approximation thereof worsens greatly at any other part.

As a result, although exact solutions are found at θ=0 degree and both the ends of θ=±90 degrees, the original purpose or the obtainment of all beams required for creating the image of the oblique section cannot be attained. It is therefore necessary to set balanced conditions for the beams, and the flow of the processing indicated above ought to hold under such conditions. Embodiments will be described below.

IV. Supplement

Now, assuming that only one oblique section as stated above has been fixed and that parallel data (theoretically, an exact solution) in the direction of θ=90 degrees shown in FIG. 8B have been obtained, let's consider a case where, while the direction of the line of sight is being turned round from θ=0 to θ=90 degrees, CP conversion operations are performed by adjusting conditions as to the respective directions. An angle at which the oblique section is seen changes depending upon θ, and the tangent thereof is given by (tan κ×sin θ). Therefore, when the CP conversion operations are successively performed in conformity with the angle, exact parallel beams are obtained in succession.

However, there are such problems (1) that, as θ becomes small, the angle of the direction of the line of sight also becomes small, so the pseudo closed domain D becomes large, and (2) that CP conversion calculations which are executed by changing conditions each time the oblique section is determined, as stated above, necessitate enormous computations. If the speed of a computer is sharply enhanced still more, and if an algorithm is rearranged to become conciser, even such processing will be possible. At present, however, the approach cannot be said practicable.

[First Embodiment]

I. Necessary Conditions

In order to complete beams necessary for image creation by employing acquired cone beam data and converted parallel beam data, the angle κ of a virtual oblique section and the angle κ' of the direction of the line of sight for parallel beams must be carefully set. The foregoing example corresponds to the case of setting κ=κ' at 9.04 degrees. Conditions to be satisfied are as arranged below.

(1) A certain wide range is covered as the acquired cone beam data hold a suitable approximation precision even outside the vicinity of that direction (θ=0) of a source in which an oblique section has been set.

(2) A certain wide range is covered as calculated converted parallel beams hold a suitable approximation precision even in directions other than the direction of θ=90 degrees.

(3) When both cone beams and the parallel beams are combined, all beams required for creating the image of the oblique section can be obtained.

II. Formulation

In order to estimate the approximation precisions of approximate data relative to virtual data, a source trajectory, a virtual plane, the various approximate data, etc. are formulated.

In the formulation, the tilt angle of the oblique section is denoted by κ, and the tangent thereof by τ, while the direction in which CP conversion is performed (the direction of the line of sight of the parallel beams) is denoted by κ' (refer to FIG. 19A), and the tangent thereof by τ'. When the angle κ is determined, the shape of the source trajectory is determined, and the shape of a pseudo closed domain D is determined. This domain becomes a region where the converted parallel beams are calculated. The direction of the line of sight is set at a direction which is rotated by an angle δ from a direction orthogonal to a point (θ=0 degree) at which the oblique section has been determined (refer to FIG. 7B).

Now, the details will be described. Here, data to be used as the approximate data are calculated.

(1) Oblique Section

The trajectory of the source having a helical function is expressed using the parameter θ.

Now, the radius of the trajectory of the source is normalized to "1 (one)", and a helical pitch to "1".

The locus of the source is defined as follows:

$$\left. \begin{array}{l} s\theta := (\cos\theta, \sin\theta, \theta/2\pi) \text{ Locus of Source} \\ Z\theta := (0, 0, \theta/2\pi) \\ R\theta := (\cos\theta, \sin\theta, 0) \end{array} \right\} \text{Expressed through Decomposition as } S\theta = z\theta + R\theta \quad (1)$$

On this occasion, S'θ being the differential of Sθ serves as one reference for determining the oblique section:

$$S'\theta = (-\sin\theta, \cos\theta, 1/2\pi)$$

A general expression including also angles other than $1/2\pi$ becomes:

$$\kappa\theta = (-\sin\theta, \cos\theta, \tan\kappa) \quad (2)$$

Here, tan κ=τ holds as stated above.

The normal vector (x, y, z) of the oblique section (virtual plane) determined by Rθ and κθ is expressed by:

$$-x \sin\theta + y \cos\theta + \tau z = 0 \quad (3)$$

$$x \cos\theta + y \sin\theta = 0 \quad (4)$$

When these equations are solved, the following is obtained:

$$(x, y, z) = (\sin\theta, -\cos\theta, 1/\tau) \quad (4)'$$

This equation is normalized as follows:

$$(x_0, y_0, z_0) = \frac{\tau}{\sqrt{\tau^2+1}} \left( \sin\theta, -\cos\theta, \frac{1}{\tau} \right) \quad (5)$$

Since the Z-coordinate of the source is Z=θ/2π, the distance d between the oblique section and the origin becomes:

$$d = \theta/(2\pi\sqrt{\tau^2+1}) \quad (5)'$$

From the above equation (3), accordingly, the virtual plane is given by:

$$x\sin\theta - y\cos\theta + \frac{1}{\tau}z = \frac{\theta}{2\pi\tau} \quad (6)$$

(2) Approximate Parallel Beam Data

As a tangential plane or a nearly tangential plane at the locus Sθ, the oblique section has been defined as stated above. Now, an oblique plane which is determined by θ=0 will be especially considered. Even then, the generality will not be lost in the ensuing discussion. A virtual plane in this case is denoted by $T_0$.

The tilt of the direction in which CP conversion is performed (the tilt of the direction of the line of sight) is denoted by τ'=tan κ'. Besides, κ=δ is assumed. Among these parallel beam groups (parallel vector groups), one nearest to the virtual plane $T_0$ is determined by steps stated below.

A projection vector in the δ direction (a vector in the direction of the line of sight) can be computed by putting θ=δ in the above equation (2). In case of κ'δ, the following is obtained:

$$\kappa'\delta = (-\sin\delta, \cos\delta, \tan\kappa') \quad (7)$$

In view of the above equation (6), the virtual plane $T_0$ at θ=0 is expressed as:

$$z = \tau y \quad (8)$$

Letting V (=(x, y, z)) denote a vector which is orthogonal to κ'δ within the virtual plane $T_0$, the following holds:

$$-x \sin\delta + y \cos\delta + \tau' z = 0$$

When this equation has the above equation (8) substituted thereinto and is arranged, the following is obtained:

$$x = \frac{\cos\delta + \tau\tau'}{\sin\delta} y \quad (9)$$

Accordingly, the magnitudes of the x and y components of the vector V have the following relation:

$$\sqrt{x^2+y^2} = \frac{|y|}{|\sin\delta|}\sqrt{1+2\tau\tau'\cos\delta+\tau^2\tau'^2}$$

Since the magnitude of the z component of the vector V is $z=\tau y$ in view of the above equation (8), a tilt $\phi$ which this vector V defines relative to an (x, y) plane is given by:

$$\phi=|\tau\sin\delta|/\sqrt{1+2\tau\tau'\cos\delta+\tau^2\tau'^2} \quad (10)$$

Originally, a tangential direction in the $\delta$ direction is taken with reference to:

$$\delta/2\pi \quad (11)$$

Therefore, the tilt of Equation (10) is set using Equation (11) as an intercept. Thus, the parallel beam data set becomes usable as approximate data.

(3) Estimation of Error

Assuming that the data in the above section (2) are actually existent as calculatable data, the error of the approximation on that occasion is estimated. In this case, the error is the difference between the tilt $\tau'$ and a tilt $\tau\cos\delta$ obtained in such a way that the virtual plane $T_0$ of the tilt $\kappa$ is seen by changing the line of sight to the amount of $\delta$. The tangent of the difference as given below is set as the index e of the error:

$$e=\tan(\tan^{-1}(\tau')-\tan^{-1}(\tau\cos\delta)) \quad (12)$$

Besides, which of data are picked out from within the calculated parallel beam group and are used as the approximate data is given by the above equations (10) and (11). Actual examples in which the errors have been estimated, will be described below.

III. Details of Embodiment

If all the beams necessary for creating the image of the oblique section can be obtained by combining the acquired cone beam data and the converted parallel beam data, and how large the errors are on that occasion, have been studied on several values of the parameters $\kappa$ and $\kappa'$ on the basis of the above formulation.

One resulting example is $\kappa=10.5$ degrees and $\kappa'=9.5$ degrees.

By the way, diagrams to be exemplified below have been obtained under the conditions that the radius of the rotation of the source is 600 mm, and that the detector is arranged with a fan angle of 50 degrees on a circular arc which is depicted around the source and which has a radius of 1100 mm.

Accordingly, the computations have been executed under the condition that an FOV is set at 600×sin 25°=253 mm×2≈500 mm.

Figure 12A:
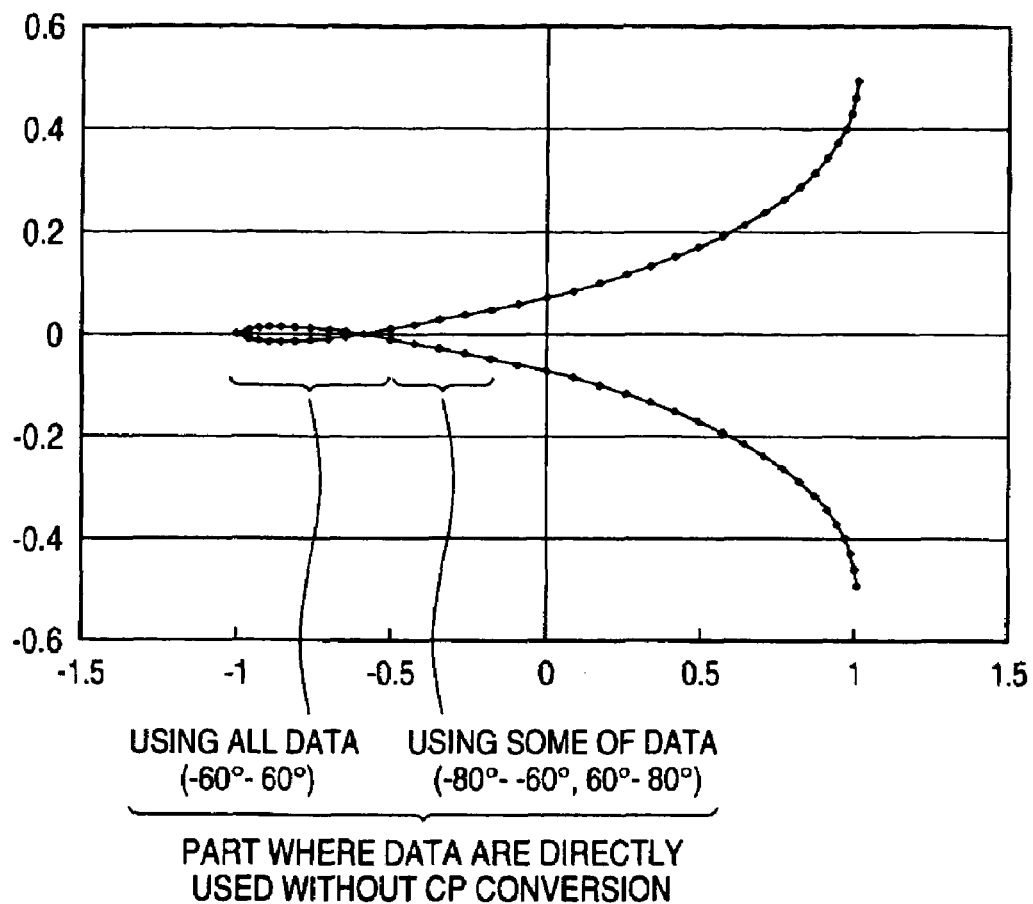

FIG. 12A shows the situation of the source trajectory seen in the direction of the line of sight. Herein, the axis of abscissas represents the direction (direction of θ=0) of an axis which is orthogonal to the direction of the line of sight and the axis of the rotation of the source, while the axis of ordinates represents a direction which is orthogonal to the direction of θ=0 and the direction of the line of sight. The diagram has been depicted in such a way that a diagram corresponding to FIG. 7A is obtained through computations at every 5° of the source rotation as to the case of $\kappa'=9.5$ degrees, whereupon the computed values are plotted. It is visually understood that the acquired cone beam data are favorably approximate to the oblique section at a part where they are directly used without the CP conversion.

Figure 12B:
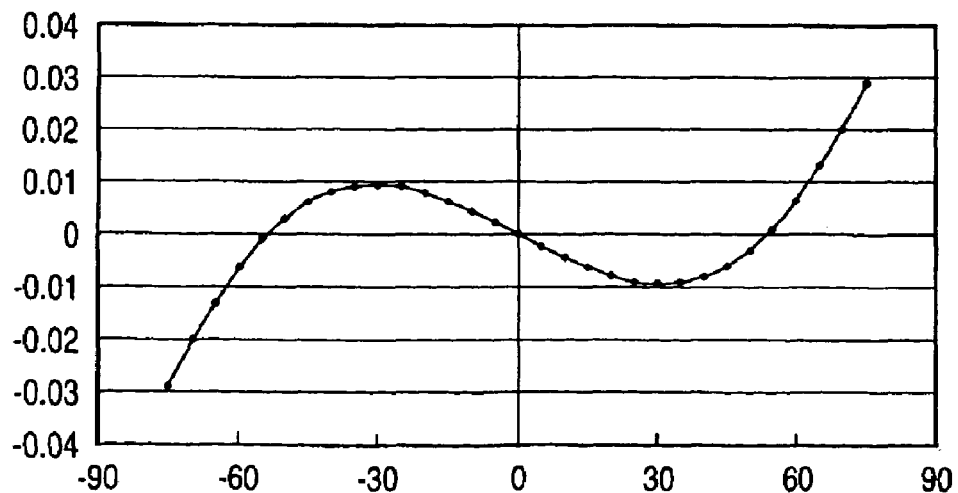
FIG. 12B is a diagram showing the estimation of errors.
Figure 13:
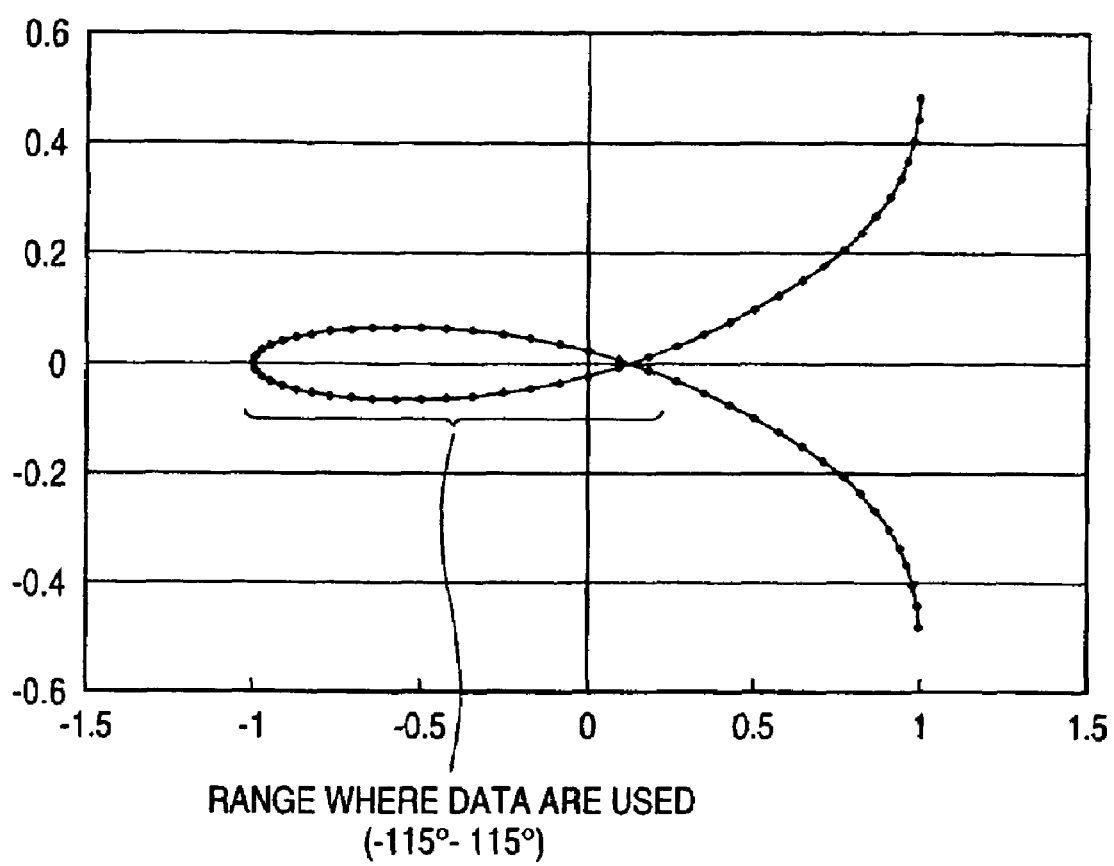
FIG. 13 is a diagram showing a source trajectory as viewed in the direction of the line of sight, on the same scale as in FIG. 12A, in the case of a prior-art example (κ=κ'=15.3 degrees)

FIG. 12B is a diagram in which the axis of abscissas represents the angle (degrees) of the source, while the axis of ordinates represents the deviation of the source from the virtual oblique section, and from which it is seen that the error is about 0.01 within the source angle of 60 degrees. In order to compare the errors of approximations, FIG. 13 shows a source trajectory seen in the direction of the line of sight in a prior-art example, in correspondence with FIG. 12A. The prior-art example corresponds to a case where, in the prior-art oblique section method wherein data necessary for half reconstruction are all supplied using only fan beam data extracted from cone beams, the parameter $\kappa'$ is equal to the parameter $\kappa$ and is 15.3 degrees as a condition for minimizing the error in the required range of the beam data. The error in the case of employing this scheme is about 0.07. When FIG. 12A and FIG. 13 are compared, it is visually understood that the error is sharply improved.

Figure 14A:
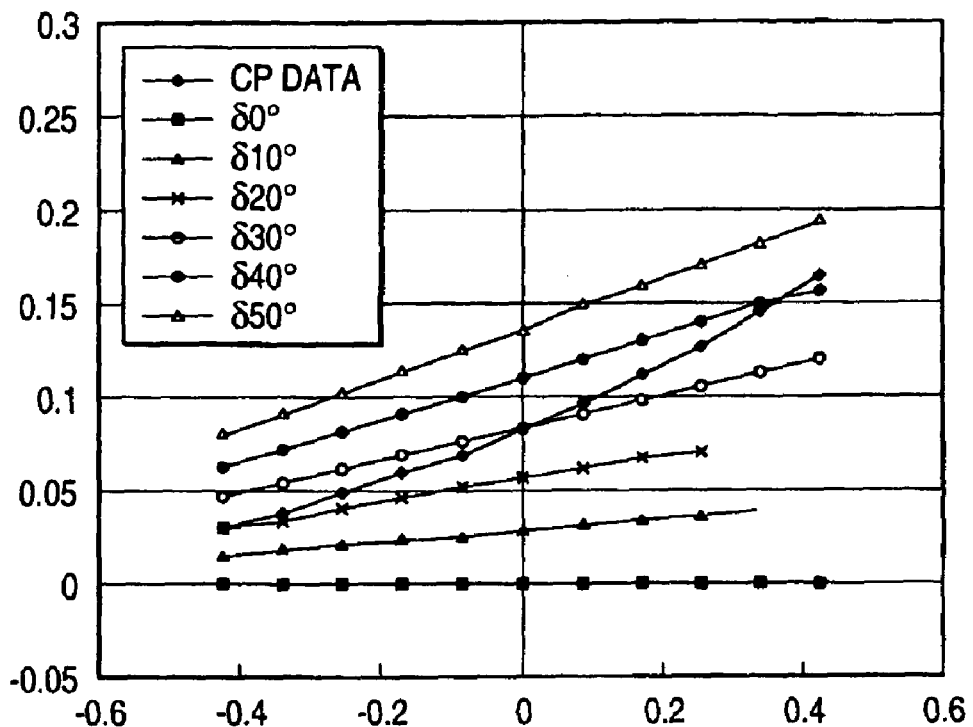

FIG. 14A is a diagram in which the existent range or calculatable range of parallel beams (that is, the shape of the pseudo closed domain D), and the positions of approximate parallel data found in the above section "formulation" (a straight line given by Equations (10) and (11) in the formulation) have been obtained as to $\kappa=10.5$ degrees and $\kappa'=9.5$ degrees. Here, the axis of abscissas and the axis of ordinates are the same as in FIG. 12A. The upper part of a graph in a range of −0.423 through 0.423 (0.423≈cos 25°, 25°=fan angle/2) in FIG. 12A corresponds to "CP data" in FIG. 14A. The parallel beams are calculatable in a part which underlies the straight line.

Figure 14B:
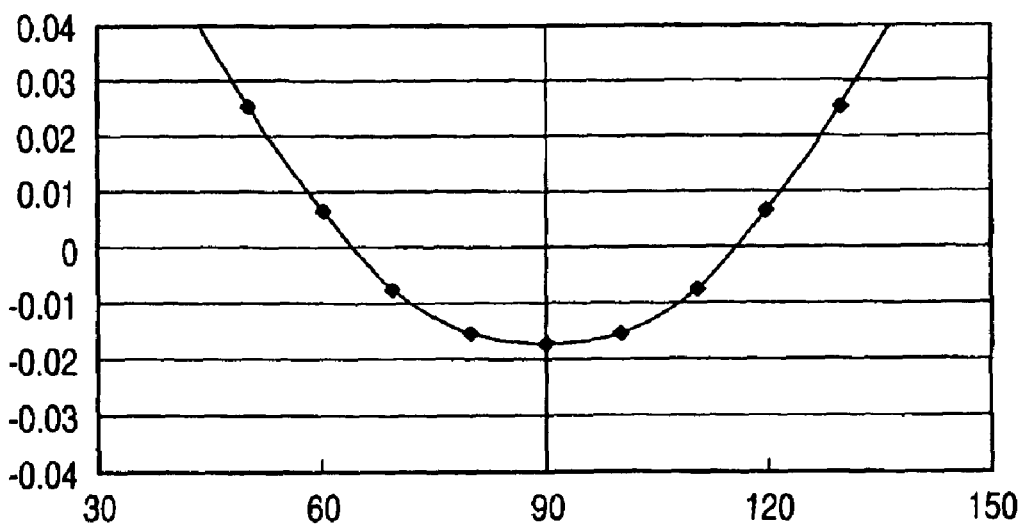
FIG. 14B is a diagram showing the estimation of errors.

FIG. 14B is a diagram showing the index e of the error (Equation (12) in the above section "formulation").

Figure 15:
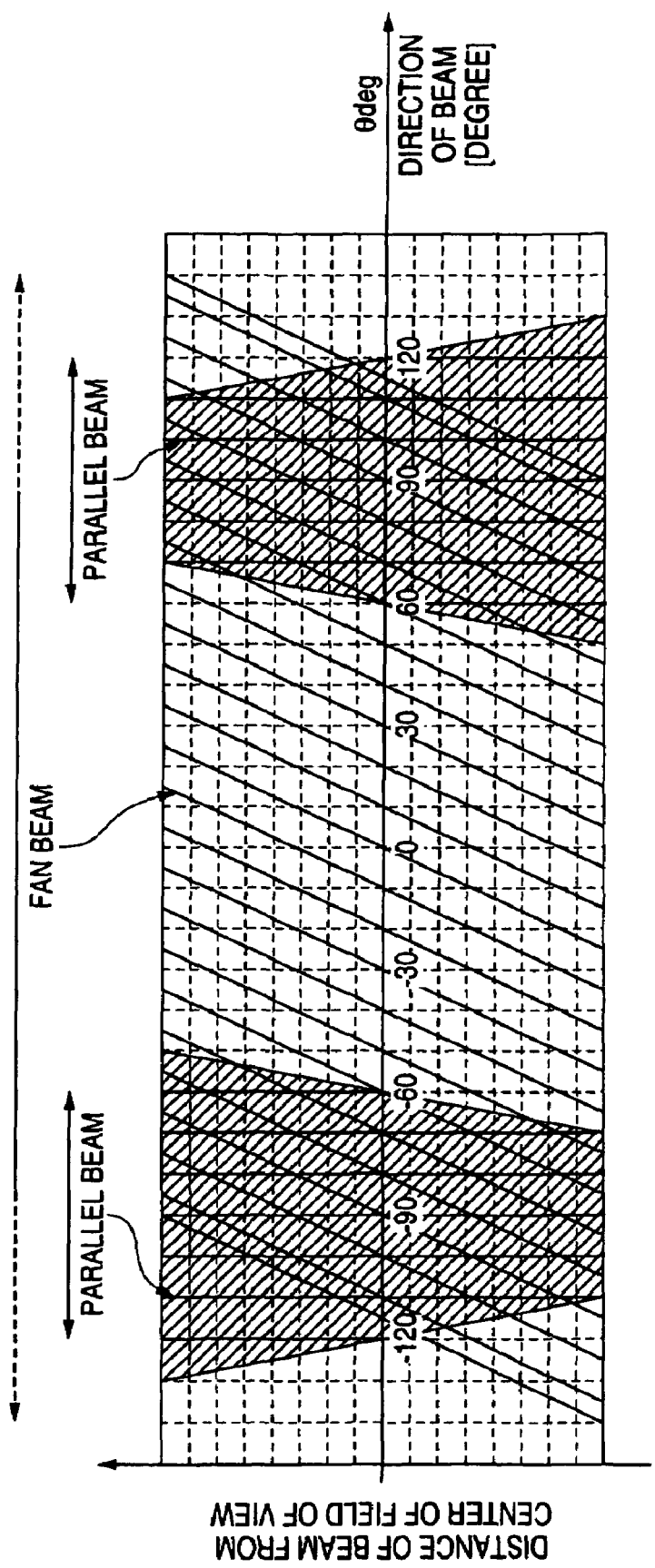
FIG. 15 is a diagram showing the existent ranges (calculatable ranges) of fan beams and parallel beams in the case of the first embodiment (κ=10.5 degrees, κ'=9.5 degrees)

Now, the existence ranges of the two sorts of data; fan beams and parallel beams are schematically shown in FIG. 15. Each fan beam is a part of a sinusoidal curve within a range of ±25 degrees (though it seems to be a straight line). The fan beams exist in a wide range, and the errors thereof gradually enlarge as shown in FIGS. 12A and 12B. The parallel beams are determined by the shape of the pseudo closed domain D. The parallel beam data are computed from, so to speak, "opposite beam groups", and the parallel beam data within right and left "trapezoidal regions" in FIG. 15 represent the same ones.

In the present invention, the beam data of smaller errors are adopted in both the data sets so as to create an image, or they are endowed with larger weights so as to create an image.

Figure 16:
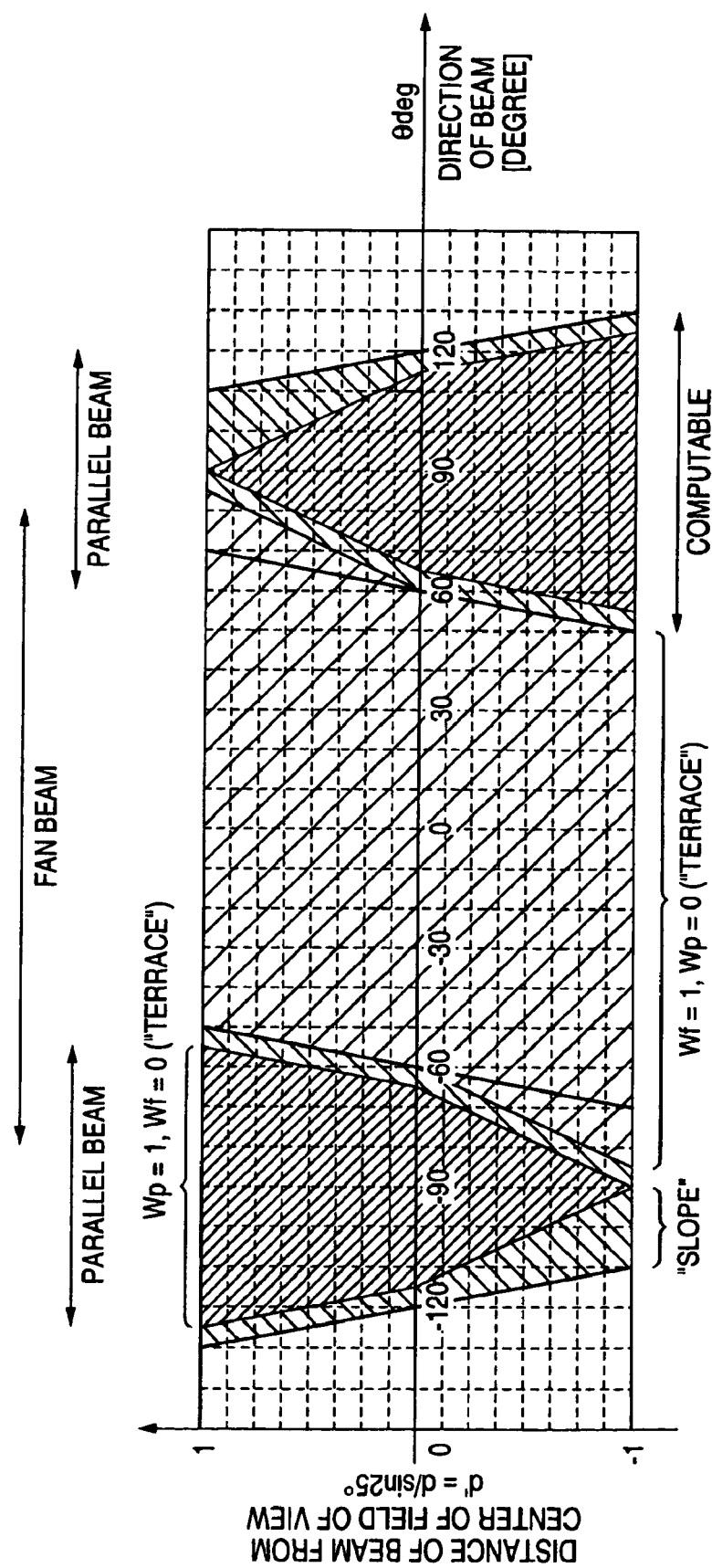
FIG. 16 is a diagram showing examples of weighting functions in the cases of respectively reconstructing fan data and parallel data in the first embodiment (κ=10.5 degrees, κ'=9.5 degrees) shown in FIG. 15.

Examples of weighting functions for the data shown in FIG. 15 will now be explained. The situation is shown in FIG. 16. As indicated by equations below, a part of sparse hatched lines corresponds to $w_f=1$ and $w_p=0$, whereas a part of dense hatched lines corresponds to $w_p=1$ and $w_f=0$. Besides, the intermediate region between the parts is a part where weights change linearly. The weighting functions are in such a shape that they repeat themselves while being inverted relative to the distances d of the beams from the origin every 180 degrees.

Examples of Weighting functions: (−90≦θdeg≦90)

(1) Weighting Function $W_f(\theta$ deg, d) of Fan Beam

For d≧0;

$w_f(\theta$ deg, $d)=0$, if θ deg≦10×d−65

$w_f(\theta$ deg, $d)=(\theta$ deg−(10×d−65))/5, if 10×d−65≦θ deg≦10×d−60

$w_f(\theta \text{ deg}, d)=1$, if $10 \times d-60 \leq \theta \text{ deg} \leq 25 \times d+60$ $w_f(\theta \text{ deg}, d)=(\theta \text{ deg}-(25 \times d+60))/5$, if $25 \times d+60 \leq \theta \text{ deg} \leq 25 \times d+65$ $w_f(\theta \text{ deg}, d)=0$, if $\theta \text{ deg} \leq 25 \times d+65$ For $d<0$;

$w_f(\theta \text{ deg}, d)=0$, if $\theta \text{ deg} \leq 25 \times d-65$ $w_f(\theta \text{ deg}, d)=(\theta \text{ deg}-(25 \times d-65))/5$, if $25 \times d-65 \leq \theta \text{ deg} \leq 25 \times d-60$ $w_f(\theta \text{ deg}, d)=1$, if $25 \times d-60 \leq \theta \text{ deg} \leq 10 \times d+60$ $w_f(\theta \text{ deg}, d)=(\theta \text{ deg}-(10 \times d+60))/5$, if $10 \times d+60 \leq \theta \text{ deg} \leq 10 \times d+65$ $w_f(\theta \text{ deg}, d)=0$, if $\theta \text{ deg} \leq 10 \times d+65$ (2) Weighting Function $w_p(\theta \text{ deg}, d)$ of Parallel Beam $w_p(\theta \text{ deg}, d)=1-w_f(\theta \text{ deg}, d)$ The weighting function originally depends upon parameters such as τ and τ'. Although a trapezoidal shape including a "terrace" and "slopes" has been exemplified here, the weighting function ought to be optimized in adaptation to the characteristics of the image of an actual subject or patient and to the purpose of use thereof.

In the diagram, the direction of the beam angle is denoted by θ, and the distance of the beam from the origin is denoted by d. The distance d is ±0.423 because of the source radius of 1 and the fan angle of ±25 degrees. The distance d as normalized to ±1 is let be d'. Then, d'=d/sin 25° holds. It is originally considered that the weighting function is conformed to a geometry extending along the sinusoidal curve of the fan beam, or a geometry such as the shape of the CP conversion region (a region which is not trapezoidal, but which is surrounded with part of a curve with the helix seen obliquely). For the sake of brevity, however, the domain of the weighting function has been determined with approximate straight lines or segments here. Of course, the weighting may well be of any smooth function unlike the linear function of the equations indicated here.

Using the weighting functions, the generation unit 31c for a parallel section group as is included in the hybrid image reconstruction system 31 executes image reconstruction as stated below. As one method for the image reconstruction, convolution back projection reconstruction (CBP reconstruction) or filtered back projection reconstruction (FBP reconstruction) based on parallel beams is executed in such a way that fan beam data are converted into parallel beams (fan beam—parallel beam conversion), whereupon the resulting parallel beams are weighted and are subjected to weighted additions with the fan beams. The method proceeds along the flow charts shown in FIGS. 10A and 10B.

[Second Embodiment]

Data acquisition, CP conversion processing, the calculations of weighting functions, etc. are the same as in the first embodiment. In the second embodiment, the last image reconstruction portion is different. After fan beam data are multiplied by the weights $w_f$ indicated in the first embodiment, ordinary reconstruction is executed using the fan beams. On the other hand, parallel beams after CP conversion are multiplied by the weighting function $w_p$, and parallel beam reconstruction is executed. Regarding directions in which quite no data exist, back projection calculations may well be omitted. The reconstructions concerning the two sorts of data are executed by different calculating algorithms, but both the algorithms afford equivalent calculations. Accordingly, a correct image can be obtained even when intermediate images, in a sense, are created for the respective sorts of data and are thereafter added. The flow of the processing in this embodiment is as shown in FIG. 11.

This method can be said a new idea or methodology not having hitherto been reported, because there has never been the concept of reconstructing an image on the basis of two sorts of original data.

In a more general expression, the method indicated here can be said a method characterized in that fan beam data and parallel beam data are respectively multiplied by two weighting functions which are the divisions of a function "1" identically becoming 1 (one), on the space of a beam set of {the tilt angle of a beam}×{the distance of the beam from the origin} or a beam set equivalent thereto, that fan beam reconstruction processing and parallel beam reconstruction processing are respectively executed, and that reconstructed images thus obtained are synthesized, whereby a final reconstruction image is formed.

[Third Embodiment]

As commented at the last of the outline preceding the first embodiment, a solution with better approximation is obtained when the tilt angle of parallel beams is changed depending upon the direction of the line of sight.

Although the single tilt angle is representatively used in the first and second embodiments, a method employing two angles will be described here. More specifically, an example of κ=10.5 degrees and κ'=9.5 degrees and an example of κ=10.5 degrees and κ2'=8 degrees will be explained. Parallel beams calculated in the pair of κ=10.5 degrees and κ'=9.5 degrees correspond to the first embodiment, and data calculated in the pair of κ=10.5 degrees and κ2'=8 degrees form an essential element added thereto. In other words, the method consists in the idea that the latter data are used to compensate for a region which is difficult to be covered with the former data, or a region in which errors are large.

Figure 17A:
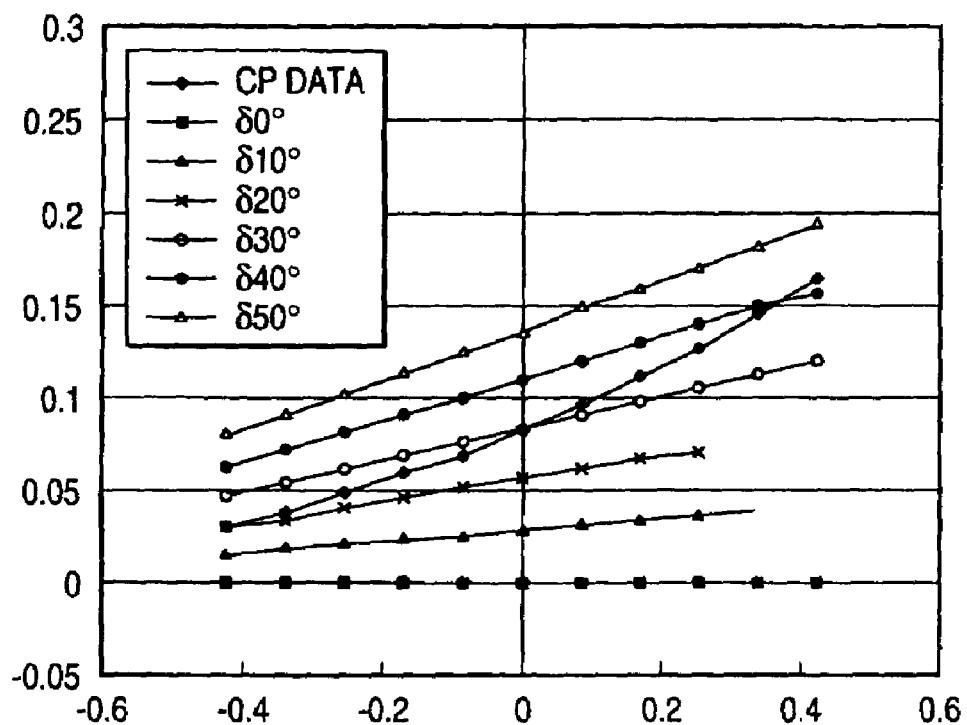
Figure 17B:
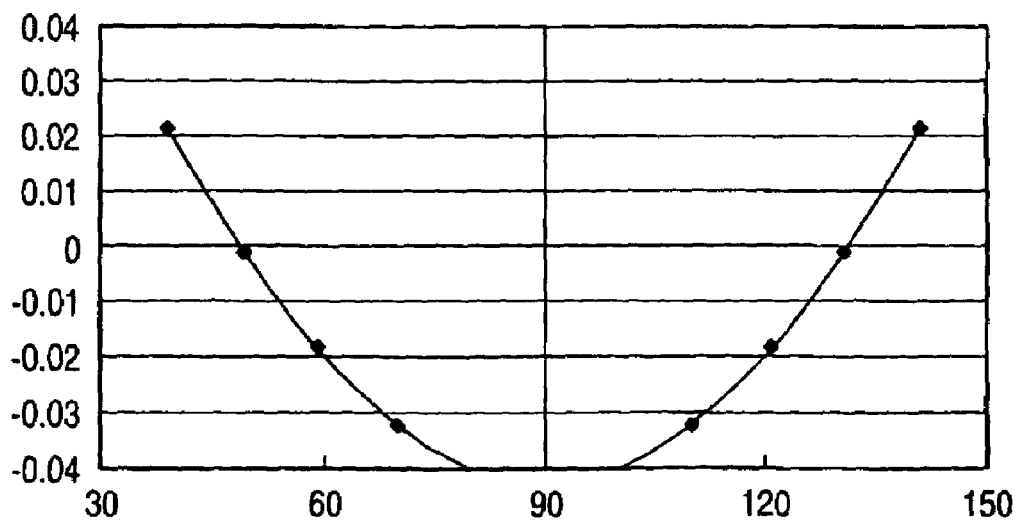
FIG. 17B is a diagram showing the estimation of errors.
Figure 18:
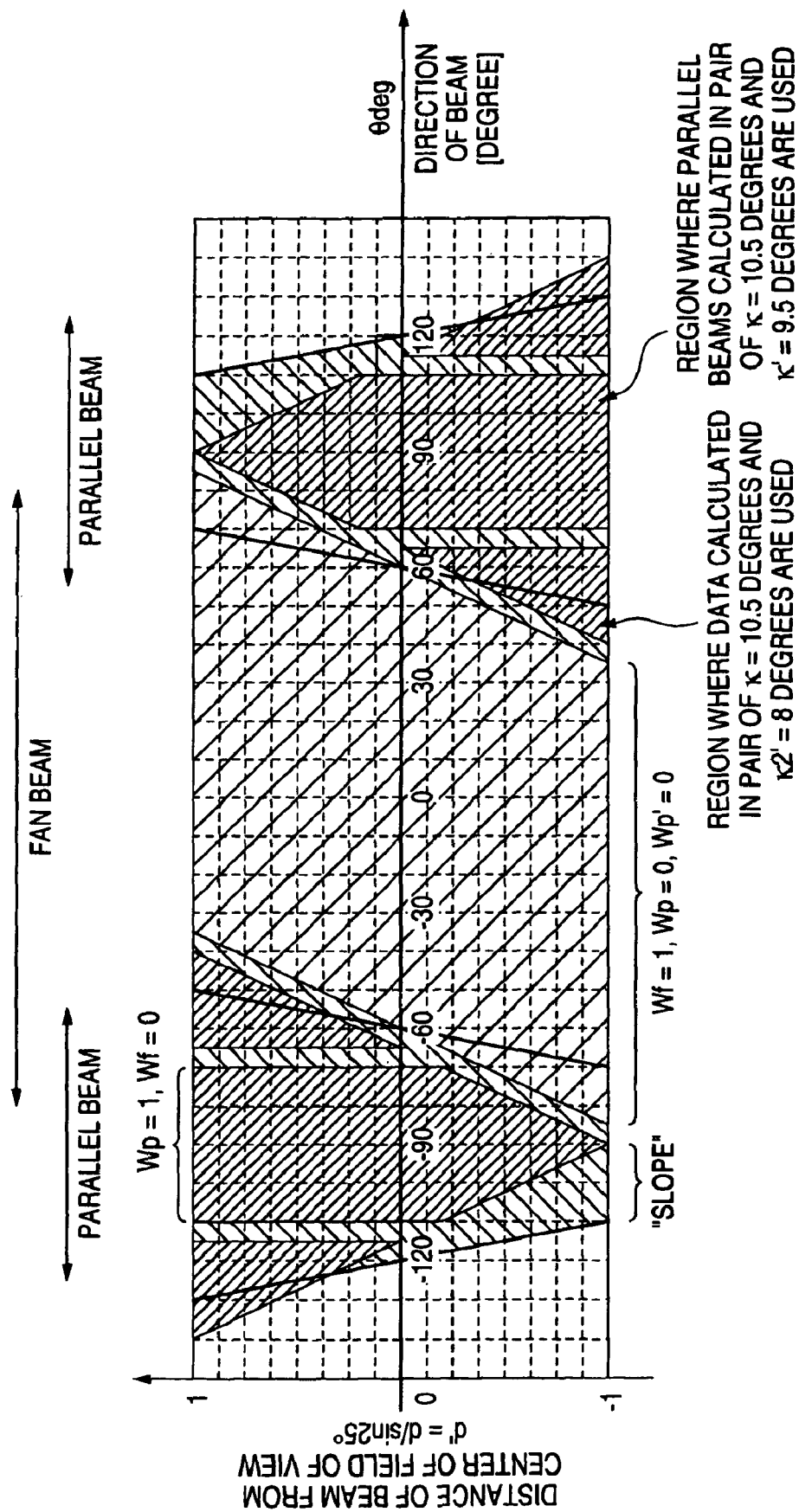
FIG. 18 is a diagram showing the existent ranges of fan beams and parallel beams in the case of the second embodiment (κ=10.5 degrees, κ'=9.5 degrees, κ"=8 degrees)

FIGS. 17A and 17B show the generatable range of parallel beams in the pair of κ=10.5 degrees and κ2'=8 degrees, as well as approximate data, and the estimation of errors, respectively. Besides, FIG. 18 shows a range (weighting functions) in which fan beams and two parallel beam groups are used on the basis of the above idea, in a shape corresponding to FIG. 16. In this embodiment, a region where the parallel beams are difficult to calculate under the conditions of κ=10.5 degrees and κ'=9.5 degrees and where the fan beam data directly approximated have large errors is covered with the data of κ=10.5 degrees and κ2'=8 degrees.

Also in this case, it is possible to adopt the method in which the fan beams are all converted into the parallel beams as in the first embodiment, or the method in which the fan beams and the parallel beams are respectively subjected to the weighted image reconstructions, followed by the synthesis of the individual images, as in the second embodiment.

[Fourth Embodiment]

Next, FIGS. 19A and 19B show an embodiment wherein the scheme of the present invention incorporates thereinto the idea that projections are made in directions in which X-ray beams have passed at the individual points of a reconstruction plane in the same manner as in the TCOT method being a prior-art method.

FIG. 19A is a diagram for explaining a parallel beam group (actually, each beam has a two-dimensional spread existing also in a direction orthogonal to the sheet of the drawing), while FIG. 19B is a diagram for explaining a cone beam group. Although the approximation based on unidimensional parallel beams or fan beams passing through the center of the radiographing field of view has been mainly described in the above, beams corresponding to the individual points are selected in this embodiment. By way of example, beams a and b passing through points A and B in FIG. 19A are respectively selected for these points. Since the original parallel beam or cone beam exists also in the direction orthogonal to the sheet of the drawing, the illustrated beam represents a plurality of parallel beams or fan beams arrayed unidimensionally, not a single beam.

The idea may well be directly applied to the prior-art helical oblique section reconstruction method or the known technique called "ASSR method". That is, in the helical oblique section reconstruction method or the ASSR method, corresponding beams are selected at individual points. In this case, the case of FIG. 19A is not existent, and only the case of FIG. 19B is actually existent.

[Fifth Embodiment]

Figure 20A:
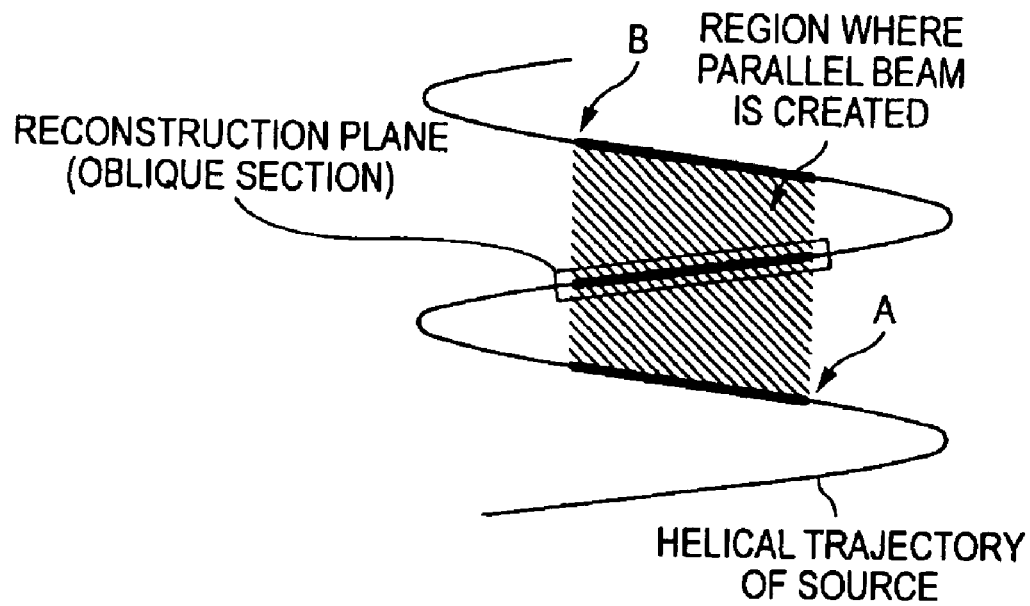
FIGS. 20A–20C are diagrams for explaining parallel beam data for use in full reconstruction.
Figure 20B:
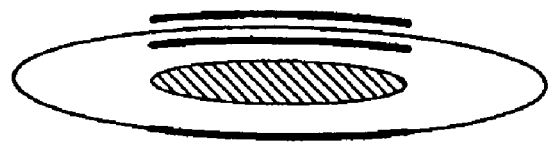
Figure 20C:

One technique for expanding the half reconstruction thus far detailed, into full reconstruction, will be described with reference to FIGS. 20A–20C. FIG. 20A shows parallel beam data for use in the "full reconstruction". The technique is a method wherein two opposite beams corresponding to beams which oppose to fan beam lying in touch with an oblique section are used for image creation.

In actuality, a parallel beam group orthogonal to the sheet of the drawing can be calculated at the part of "region where parallel beam is created" in FIG. 20A can be calculated using beams from all source positions from a point A to a point B on a trajectory, by the same method as shown in FIG. 8A–FIG. 9. The situation of FIG. 20A is schematically shown in FIGS. 20B and 20C.

Referring to FIG. 21, a part within a broken line is the part of the "half" reconstruction detailed in and before the third embodiment above. A pattern within the lowermost circle in FIG. 21 indicates that fan beams are used in the vicinity of a tangential line to a source as determines an oblique section. "Opposite beams" are used within the range of directions which differ substantially ±90°. Also data are symmetrically used in this part. In actuality, two data in the directions of 3 o'clock and 9 o'clock in the figure represent the same ones. As stated above, this part enclosed with the broken line in the figure corresponds to the half reconstruction. In directions in which the source is further rotated, parallel beams are created by the method shown in FIGS. 20A–20C. In this way, data for 360 degrees can be obtained, and the half reconstruction can be expanded to the full reconstruction.

[Modifications]

In an actual apparatus, a diagnostic table might be moved in use in both the directions of the direction of inserting it into a CT gantry and the direction of retreating it therefrom. Besides, regarding the rotational direction itself of a source, two directions including reversal are considered. In this case, the relative helical motion of the source with respect to a subject or patient is in mirror symmetry, and the above data processing (including the creation of approximate projection data, the coordinates of reverse projection calculations, etc.) is entirely in mirror symmetry. It is naturally necessary to cope with the mirror symmetry.

Further, even in a case where a tabletop performs a reciprocating motion, the method of the present invention can be applied. When the patient is repeatedly radiographed by, for example, dynamic scan, movements different from those in the embodiments described above are performed in such a case where a helical pitch lowers gradually to come to a standstill once at the stage of the turn of the tabletop motion, and where the table top subsequently moves in the opposite sense. However, the idea of generating the fan beam and the opposite beams on the plane along the tangential line to the trajectory and reconstructing an image by using either or both of the beams can be similarly applied.

Moreover, a spatial resolution can be enhanced by employing the method of the present invention and a shift mechanism conjointly. By way of example, it is assumed to "shift" the radius of the rotation of the source from 600 mm in the foregoing example to 400 mm being ⅔. In this method, in interlocking with the shift, the movement magnitude of the diagnostic table per revolution of the source changes from 15 mm to 10 mm being ⅔, and the thickness of a slice becomes ⅔. Although the interlocking is not always necessary, it is the most efficient to enhance the resolution in the whole image including a slicing direction.

(Other Embodiments)

(1) Image Reconstruction and Calculation/Data Processing of Volume Data

In the prior-art method "helical oblique section reconstruction method", reconstruction may be executed concerning an x-axis and a y-axis perpendicular to a z-direction, as the coordinate system of the reconstruction. While a reconstruction plane has a slight tilt, an image with the reconstruction plane viewed in the z-direction is obtained. Also in the present invention, when coordinates for calculating parallel beams are carefully set, it can be dispensed with to take two-dimensional coordinates within the virtual plane again.

Thus far, the acquisition of a single slice has been explained. In order to create continuous "adjacent planes", the position of an approximate "half helix" maybe shifted little by little. By way of example, in a case where 8 slices are to be obtained per revolution of a source, images may be successively acquired under the condition that a virtual plane is set while the position of the approximate helix is being shifted every 360 degrees/8=45 degrees. Such processing can be executed likewise to the prior-art helical oblique section reconstruction method.

Since the series of images obtained are non-parallel, it is necessary to extract any two-dimensional image such as sections parallel to each other or a sectional conversion image including a curved section conversion image. Such data processing can be executed likewise to the prior-art method.

(2) Geometry in This Specification

Since, in the description of this specification, various calculations are executed by setting both the radius of the rotation of a source and the helical pitch of the source at "1 (one)", they are somewhat different from calculations under actual conditions. By way of example, in a case where the helical pitch of at most 16 arrays or 32 arrays is much smaller than the radius of the rotation of the source, computed values become different from the foregoing. The scheme of the present invention, however, can be applied in a similar procedure.

(3) Theoretical Intermediate Data

Algorithms for calculating theoretical exact solutions are thought to be further improved or rearranged in the future also in point of data processing. However, a reconstruction plane along a tangential line to the trajectory of a source as noticed in the method of the present invention has the feature that projection beam data in the vicinity of the tangential line are very good approximate data. The feature is exploited to the utmost in the method of the present invention, and the method is thought to be highly useful in a medical image diagnostic equipment whose subject is a mobile living body.

Besides, apart from the geometrical type indicated in this specification, there will be various exact solutions which are mathematically equivalent. Although the intermediate data based on the Schaller et al. scheme have been exemplified in this specification, such intermediate data will be described in different expressions by future theoretical progresses. In applying the method of the present invention, accordingly, various modified techniques are considered. To the last, however, the subject matter of the present invention consists in that image reconstruction is executed by combining acquired cone beam data and different intermediate calculated data.

Thus far, in three-dimensional CT whose practical use has been started at present, especially in 3D helical CT based on cone-beam geometry, there has been proposed a practicable technique which employ only data of still higher precision as are necessary and sufficient to the utmost.

Incidentally, the present invention is not restricted to the foregoing embodiments and modifications typically exemplified, but one skilled in the art can modify and alter them into various aspects within a scope not departing from the subject matter of the invention, on the basis of contents described in the appended claims. Such alterations and modifications shall also belong to the claimed scope of the present invention.

What is claimed is:

1. A computed tomography apparatus comprising:
   a data acquisition unit configured to acquire projection data of a radiographic region within a subject using a multirow detector; and
   an image reconstruction unit configured to reconstruct an image of the radiographic region on the basis of both two-dimensional projection data which are extracted from the projection data acquired by said data acquisition unit, and additional two-dimensional data which are extracted from three-dimensional data calculated on the basis of three-dimensional partial data extracted from the projection data acquired by said data acquisition unit.

2. A computed tomography apparatus as defined in claim 1, wherein the additional two-dimensional data are parallel projection data.

3. A computed tomography apparatus as defined in claim 1, wherein said image reconstruction unit reconstructs the image of the radiographic region on the basis of fan beam data which are obtained from cone beam data as the projection data, and two-dimensional parallel beam data which are obtained from three-dimensional parallel beam data as the additional two-dimensional data.

4. A computed tomography apparatus as defined in claim 1, wherein:
   said data acquisition unit acquires the projection data by helical scan; and
   said image reconstruction unit extracts approximate projection data and approximate additional data as are approximate to a set reconstruction plane from the projection data and the additional data, and reconstructs the image on the basis of the respective approximate projection data.

5. A computed tomography apparatus as defined in claim 4, wherein the reconstruction plane is set as an oblique section which tilts with respect to a center axis of the helical scan.

6. A computed tomography apparatus as defined in claim 4, wherein said image reconstruction unit sets a plurality of reconstruction planes so as to be spatially continuous, and reconstructs images on the respective reconstruction planes to obtain volume data.

7. A computed tomography apparatus as defined in claim 4, wherein:
   the helical scan is performed in such a way that an X-ray source moves on a helical trajectory relatively to the subject; and
   the reconstruction plane is set as a plane which is approximate to a curved plane that is depicted by a plurality of X-ray paths while the X-ray source rotates substantially 180 degrees.

8. A computed tomography apparatus as defined in claim 4, wherein said image reconstruction unit successively generates parallel beam data sets so as to approximate beam data of a plurality of reconstruction planes set along a helical trajectory, extracts beam data sets approximating a predetermined reconstruction plane from the generated parallel beam data sets, interpolates projection data sets of the predetermined reconstruction plane from the beam data sets, and reconstructs the image on the basis of the projection data sets generated by the interpolation processing.

9. A computed tomography apparatus as defined in claim 4, wherein said image reconstruction unit generates parallel beam projection data in a pseudo closed domain which is held between opposing source trajectory parts of a helical trajectory, generates approximate data for half reconstruction of the reconstruction plane on the basis of the parallel beam projection data and acquired fan beam projection data, and reconstructs the image on the basis of the approximate data.

10. A computed tomography apparatus as defined in claim 4, wherein said image reconstruction unit generates parallel beam projection data in a pseudo closed domain which is held between opposing source trajectory parts of a helical trajectory, further generates parallel beam projection data in a pseudo closed domain which is held between two opposing trajectory parts nearest to a helical trajectory that determines a tilt plane, generates approximate data for full reconstruction of the reconstruction plane on the basis of the parallel beam projection data and acquired fan beam projection data, and reconstructs the image on the basis of the approximate data.

11. A computed tomography apparatus comprising:
   a data acquisition unit configured to acquire projection data of a radiographic region within a subject using a multirow detector; and
   an image reconstruction unit configured to extract from the projection data, approximate projection data of X-ray paths that approximate a reconstruction plane not being always orthogonal to a rotational center axis of the multirow detector, and to reconstruct an image of the radiographic region on the basis of the approximate projection data;
   wherein said image reconstruction unit selects approximate fan beams or approximate parallel beams every point of the reconstruction plane, and reconstructs the image of the radiographic region using approximate beams.

12. A computed tomography apparatus as defined in claim 11, wherein the approximate fan beams or approximate parallel beams which are used every point of the reconstruction plane include a beam which includes the point.

13. A computed tomography apparatus as defined in claim 11, wherein the beam group which is used every point of the reconstruction plane consists of the approximate fan beams.

14. A computed tomography apparatus as defined in claim 11, wherein fan beams or parallel beams are used every point of the reconstruction plane, and they include a beam which approximates the point.

15. A computed tomography apparatus as defined in claim 13, wherein the approximate fan beams or approximate parallel beams which are used every point of the reconstruction plane include a beam which includes the point.

16. A computed tomography apparatus comprising:
   a data acquisition unit configured to acquire projection data of a radiographic region within a subject; and
   an image reconstruction unit configured to reconstruct a two-dimensional reconstruction image of the radiographic region on the basis of both fan beam data which are the projection data acquired by said data acquisition unit, and parallel beam data which are calculated from the fan beam data.

17. A computed tomography apparatus as defined in claim 16, wherein said image reconstruction unit generates a parallel beam data set necessary for generating the reconstruction image of the diagnostic part, on the basis of both the fan beam data as subjected to parallel conversion and the parallel beam data, and reconstructs the image of the radiographic region on the basis of the data set.

18. A computed tomography apparatus as defined in claim 16, wherein said image reconstruction unit executes a reconstruction process using the fan beam data, and a reconstruction process using the parallel beam data, respectively, and reconstructs the final image by synthesizing reconstruction images obtained by the respective processes with each other.

19. A computed tomography apparatus as defined in claim 18, wherein said image reconstruction unit multiplies the fan beam data and the parallel beam data by two weighting functions which are divisions of "1 (one)", on a space which is set by a tilt angle of a beam and a distance of the beam from an origin or on a space which is a beam set equivalent to the first-mentioned space, respectively, thereafter executes a reconstruction process using the fan beam data and a reconstruction process using the parallel beam data, respectively, and reconstructs the final image by synthesizing reconstruction images obtained by the respective processes with each other.

20. A program which causes a computer mounted on a computed tomography apparatus, to execute:
   a step of extracting two-dimensional projection data from projection data of a radiographic region within a subject as acquired using a multirow detector;
   a step of extracting three-dimensional data on the basis of three-dimensional partial data extracted from the acquired projection data;
   a step of extracting two-dimensional data from the three-dimensional data; and
   a step of reconstructing an image of the radiographic region on the basis of both the two-dimensional projection data and the two-dimensional extracted data.

21. A program which causes a computer mounted on a computed tomography apparatus, to execute:
   a step of extracting from projection data of a radiographic region within a subject as acquired using a multirow detector, approximate projection data of X-ray paths which approximate a reconstruction plane not being always orthogonal to a rotational center axis of the multirow detector; and
   a step of reconstructing an image of the radiographic region on the basis of the approximate projection data;
   wherein the reconstructing step selects approximate fan beams or approximate parallel beams every point of the reconstruction plane, and reconstructs the image of the radiographic region using the approximate beams.

22. A program which causes a computer mounted on a computed tomography apparatus, to execute:
   a step of calculating parallel beam data from fan beam data which are projection data of a radiographic region within a subject; and
   a step of reconstructing a two-dimensional image of the radiographic region on the basis of both the fan beam data and the parallel beam data.

* * * * *